US011540512B2

(12) United States Patent
Man et al.

(10) Patent No.: US 11,540,512 B2
(45) Date of Patent: Jan. 3, 2023

(54) REDUCED INHALATION HAZARD SANITIZERS AND DISINFECTANTS VIA HIGH MOLECULAR WEIGHT POLYMERS

(71) Applicant: ECOLAB USA INC., Saint Paul, MN (US)

(72) Inventors: Victor Fuk-Pong Man, Saint Paul, MN (US); Derrick Anderson, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/909,642

(22) Filed: Mar. 1, 2018

(65) Prior Publication Data
US 2018/0249704 A1 Sep. 6, 2018

Related U.S. Application Data

(60) Provisional application No. 62/465,483, filed on Mar. 1, 2017.

(51) Int. Cl.
A01N 25/02 (2006.01)
A01N 33/12 (2006.01)
C11D 17/00 (2006.01)
C11D 1/62 (2006.01)
C11D 3/37 (2006.01)
C11D 3/48 (2006.01)
A61L 2/22 (2006.01)
A61L 9/14 (2006.01)

(52) U.S. Cl.
CPC ............ A01N 25/02 (2013.01); A01N 33/12 (2013.01); A61L 2/22 (2013.01); A61L 9/14 (2013.01); C11D 1/62 (2013.01); C11D 3/37 (2013.01); C11D 3/48 (2013.01); C11D 17/0043 (2013.01)

(58) Field of Classification Search
CPC .... A01N 25/02; A01N 33/12; C11D 17/0043; C11D 1/62; C11D 3/37; C11D 3/48; A61L 2/22; A61L 9/14
See application file for complete search history.

(56) References Cited

U.S. PATENT DOCUMENTS

| | | |
|---|---|---|
| 3,644,210 A | 2/1972 | Crotty et al. |
| 3,658,988 A | 4/1972 | Scher |
| 3,779,933 A | 12/1973 | Eisen |
| 3,813,343 A | 5/1974 | Mukai et al. |
| 3,829,387 A | 8/1974 | Wise et al. |
| 4,140,516 A | 2/1979 | Scher |
| 4,214,915 A | 7/1980 | Dillarstone et al. |
| 4,314,841 A | 2/1982 | Scher |
| 4,357,351 A | 11/1982 | Fancher et al. |
| 4,425,241 A | 1/1984 | Swanson |
| 4,426,362 A | 1/1984 | Copeland et al. |
| 4,440,563 A | 4/1984 | Scher |
| 4,492,646 A | 1/1985 | Welch |
| 4,500,494 A | 2/1985 | Scher |
| 4,510,081 A | 4/1985 | Bronner et al. |
| 4,515,813 A | 5/1985 | Fancher et al. |
| 4,618,914 A | 10/1986 | Sato et al. |
| 4,647,258 A | 3/1987 | Massarsch |
| 4,654,161 A | 3/1987 | Kollmeier et al. |
| 4,673,704 A | 6/1987 | Flesher et al. |
| 4,676,920 A | 6/1987 | Culshaw |
| 4,687,121 A | 8/1987 | Copeland |
| 4,690,305 A | 9/1987 | Copeland |
| 4,767,563 A | 8/1988 | de Buzzaccarini |
| RE32,763 E | 10/1988 | Fernholtz et al. |
| 4,778,836 A | 10/1988 | Farrar et al. |
| RE32,818 E | 1/1989 | Fernholz et al. |
| 4,826,661 A | 5/1989 | Copeland et al. |
| 4,830,773 A | 5/1989 | Olson |
| 4,877,691 A | 10/1989 | Cockrell, Jr. |
| 4,898,611 A | 2/1990 | Gross |
| 4,913,775 A | 4/1990 | Langley et al. |
| 4,929,655 A | 5/1990 | Takeda et al. |
| 4,933,167 A | 6/1990 | Scher et al. |
| 4,950,725 A | 8/1990 | Flesher et al. |
| 4,956,129 A | 9/1990 | Scher et al. |
| 5,110,883 A | 5/1992 | Gartner |
| 5,120,542 A | 6/1992 | Scher et al. |
| 5,134,961 A | 8/1992 | Giles et al. |
| 5,171,783 A | 12/1992 | Gartner |
| 5,332,584 A | 7/1994 | Scher et al. |

(Continued)

FOREIGN PATENT DOCUMENTS

BG 65638 B1 4/2009
CA 1085238 9/1980

(Continued)

OTHER PUBLICATIONS

Ecolab USA Inc., "Written Opinion of the International Preliminary Examining Authority", PCT/US2018/020424, filing date Jan. 3, 2018, 7 pages, dated Feb. 7, 2019.
Nalco 625 Liquid Anionic Flocculant, Product Bulletin, Nalco Company, 3 pages, 2014.
Core Shell 61067 Paper Process Polymer, Product Bulletin, Nalco Company, 5 pages, 2014.
Plurafac LF-221 Alcohol Alkoxylate, Technical Bulletin, BASF Corporation, 1 page, 2002.
Bozetine, I., et al., "Optimization of an Alkylpolyglucoside-Based Dishwashing Detergent Formuation", Journal of Surfactants and Detergents (Dec. 2008) 11: pp. 299-305.

(Continued)

Primary Examiner — Sahar Javanmard
(74) Attorney, Agent, or Firm — McKee, Voorhees & Sease, PLC

(57) ABSTRACT

The invention provides antimicrobial compositions having reduced inhalation risks by combining ammonium compounds and polymers in combination with optional acid components, surfactants and/or additional functional ingredients. The antimicrobial compositions which have a reduced risk of inhalation. Methods of making and employing the compositions are disclosed.

8 Claims, No Drawings

(56) References Cited

U.S. PATENT DOCUMENTS

| | | |
|---|---|---|
| 5,364,551 A | 11/1994 | Lentsch et al. |
| 5,393,381 A | 2/1995 | Hund et al. |
| 5,397,506 A | 3/1995 | Groth et al. |
| 5,454,984 A | 10/1995 | Graubart et al. |
| 5,474,698 A | 12/1995 | Rolando et al. |
| 5,501,815 A | 3/1996 | Man |
| 5,518,634 A | 5/1996 | Pillai et al. |
| 5,589,099 A | 12/1996 | Baum |
| 5,601,723 A | 2/1997 | Kirk et al. |
| 5,603,776 A | 2/1997 | Lentsch et al. |
| 5,674,831 A | 10/1997 | Schulz et al. |
| 5,700,771 A | 12/1997 | Hardy et al. |
| 5,876,514 A | 3/1999 | Rolando et al. |
| 5,880,089 A | 3/1999 | Lentsch et al. |
| 5,912,207 A | 6/1999 | Scher et al. |
| 5,945,494 A | 8/1999 | Neff et al. |
| 6,103,839 A | 8/2000 | Patel et al. |
| 6,258,765 B1 | 7/2001 | Wei et al. |
| 6,294,515 B1 | 9/2001 | Baum |
| 6,294,622 B1 | 9/2001 | Barajas et al. |
| 6,485,736 B1 | 11/2002 | Shirley et al. |
| 6,530,383 B1 | 3/2003 | Rogmann et al. |
| 6,537,961 B1 | 3/2003 | Koch |
| 6,541,422 B2 | 4/2003 | Scher et al. |
| 6,544,540 B2 | 4/2003 | Van Koppenhagen et al. |
| 6,605,674 B1 | 8/2003 | Whipple et al. |
| RE38,262 E | 10/2003 | Rolando et al. |
| 6,750,190 B2 | 6/2004 | Colurciello et al. |
| 6,753,388 B1 | 6/2004 | Whipple et al. |
| 6,956,019 B2 | 10/2005 | Lentsch et al. |
| 7,271,200 B2 | 9/2007 | Scher et al. |
| 7,278,294 B2 | 10/2007 | Giles et al. |
| 7,279,455 B2 | 10/2007 | Kieffer et al. |
| 7,311,004 B2 | 12/2007 | Giles |
| 7,502,665 B2 | 3/2009 | Giles et al. |
| 7,566,448 B2 | 7/2009 | Becker et al. |
| 7,592,301 B2 | 9/2009 | Smith et al. |
| 7,665,348 B2 | 2/2010 | Giles |
| 7,742,842 B2 | 6/2010 | Giles et al. |
| 7,826,930 B2 | 11/2010 | Giles et al. |
| 8,097,687 B2 | 1/2012 | Kurian et al. |
| 8,109,448 B2 | 2/2012 | Giles |
| 8,173,159 B2 | 5/2012 | Scher et al. |
| 8,250,907 B2 | 8/2012 | Giles |
| 8,852,648 B2 * | 10/2014 | Salamone .............. A61K 33/38 424/618 |
| 8,865,632 B1 | 10/2014 | Parnell et al. |
| 8,916,508 B2 | 12/2014 | Parnell et al. |
| 9,206,381 B2 | 12/2015 | Hodge et al. |
| 2002/0037306 A1 | 3/2002 | Van Koppenhagen et al. |
| 2002/0069901 A1 | 6/2002 | Evers |
| 2002/0192340 A1 | 12/2002 | Swart et al. |
| 2003/0109403 A1 | 6/2003 | Man et al. |
| 2003/0171243 A1 | 9/2003 | Kischkel et al. |
| 2004/0010930 A1 | 1/2004 | Dolechek et al. |
| 2004/0033269 A1 | 2/2004 | Hei et al. |
| 2004/0157760 A1 | 8/2004 | Man et al. |
| 2004/0224867 A1 | 11/2004 | Colurciello et al. |
| 2006/0246242 A1 | 11/2006 | Siegel et al. |
| 2007/0043119 A1 | 2/2007 | Graeber et al. |
| 2007/0253926 A1 | 11/2007 | Tadrowski et al. |
| 2007/0264344 A1 | 11/2007 | Segura-Orsoni et al. |
| 2008/0132438 A1 * | 6/2008 | Hoffman ................ A01N 25/34 510/380 |
| 2008/0199535 A1 * | 8/2008 | Taylor .................... A01N 31/16 424/617 |
| 2008/0230624 A1 | 9/2008 | Giles et al. |
| 2008/0293615 A1 | 11/2008 | Kieffer et al. |
| 2009/0035339 A1 | 2/2009 | Istvan et al. |
| 2009/0111716 A1 | 4/2009 | Hough et al. |
| 2009/0196897 A1 | 8/2009 | Gladfelter et al. |
| 2010/0009886 A1 | 1/2010 | Smith et al. |
| 2010/0286019 A1 | 11/2010 | Scher et al. |
| 2010/0294498 A1 | 11/2010 | Svoboda et al. |
| 2010/0300044 A1 | 12/2010 | Man et al. |
| 2011/0092398 A1 | 4/2011 | Dahanayake et al. |
| 2012/0168532 A1 | 7/2012 | Giles |
| 2012/0258157 A1 | 10/2012 | Koltzenburg et al. |
| 2012/0329138 A1 | 12/2012 | Van Kaathoven et al. |
| 2013/0121944 A1 | 5/2013 | Leyrer et al. |
| 2013/0172228 A1 | 7/2013 | Bartelme et al. |
| 2013/0255729 A1 | 10/2013 | Hodge et al. |
| 2013/0284205 A1 | 10/2013 | Hodge et al. |
| 2014/0148371 A1 | 5/2014 | Man et al. |
| 2014/0148372 A1 | 5/2014 | Man et al. |
| 2015/0232793 A1 | 8/2015 | Hodge et al. |
| 2015/0307817 A1 | 10/2015 | Peitersen et al. |
| 2017/0335253 A1 | 11/2017 | Man et al. |
| 2017/0335254 A1 | 11/2017 | Man et al. |
| 2018/0042228 A1 | 2/2018 | Man et al. |
| 2018/0249704 A1 | 9/2018 | Man et al. |

FOREIGN PATENT DOCUMENTS

| | | |
|---|---|---|
| CA | 1199808 | 1/1986 |
| CA | 2101641 C | 8/1992 |
| CA | 1317875 | 5/1993 |
| CA | 2122956 | 11/1994 |
| CA | 2245537 C | 8/1997 |
| CA | 2276364 A1 | 7/1998 |
| CA | 2339013 A1 | 2/2000 |
| CA | 2376679 A1 | 3/2001 |
| CA | 2405977 A1 | 12/2001 |
| CA | 2447759 A1 | 12/2002 |
| CA | 2493361 A1 | 2/2004 |
| CA | 2512324 A1 | 1/2007 |
| CN | 103814103 A | 5/2014 |
| CN | 109153947 A | 1/2019 |
| CN | 109153948 A | 1/2019 |
| CN | 109475125 A | 3/2019 |
| DE | 69918694 T2 | 7/2005 |
| EP | 0005302 A2 | 11/1979 |
| EP | 0085327 A1 | 8/1983 |
| EP | 0202780 A2 | 11/1986 |
| EP | 0363024 A1 | 4/1990 |
| EP | 0374458 A2 | 6/1990 |
| EP | 0411218 A1 | 2/1991 |
| EP | 0523198 B1 | 1/1993 |
| EP | 0623052 B1 | 11/1994 |
| EP | 0787778 A1 | 8/1997 |
| EP | 1102834 B1 | 5/2001 |
| EP | 1103017 B1 | 5/2001 |
| GB | 2306965 A | 5/1997 |
| JP | 11510542 A | 9/1999 |
| JP | 2001503770 A | 3/2001 |
| JP | 2008519846 A | 6/2008 |
| JP | 2009111294 A | 5/2009 |
| JP | 2009296121 A | 12/2009 |
| JP | 2011511764 A | 4/2011 |
| JP | 2013533215 A | 8/2013 |
| JP | 2014512462 A | 5/2014 |
| JP | 2014530271 A | 11/2014 |
| JP | 2015535281 A | 12/2015 |
| WO | 198002024 A1 | 10/1980 |
| WO | 1989/11525 | 11/1989 |
| WO | 1992/10093 | 6/1992 |
| WO | 1992/13448 | 8/1992 |
| WO | 1993/14865 | 8/1993 |
| WO | 1997/07675 | 3/1997 |
| WO | 1997/27748 | 8/1997 |
| WO | 1997/39089 | 10/1997 |
| WO | 1998/28975 | 7/1998 |
| WO | 2000/05951 | 2/2000 |
| WO | 2000/08125 | 2/2000 |
| WO | 200005952 A1 | 2/2000 |
| WO | 2000/46327 | 8/2000 |
| WO | 2001/19509 | 3/2001 |
| WO | 2001/83879 | 11/2001 |
| WO | 200202662 A1 | 1/2002 |
| WO | 2002/48299 | 6/2002 |
| WO | 2002/100525 | 12/2002 |
| WO | 02100374 A2 | 12/2002 |
| WO | 2004010930 A2 | 2/2004 |
| WO | 2005085321 A1 | 9/2005 |

(56) References Cited

FOREIGN PATENT DOCUMENTS

| | | |
|---|---|---|
| WO | 2007104895 A1 | 9/2007 |
| WO | 2009143513 A1 | 11/2009 |
| WO | 2010091333 A2 | 8/2010 |
| WO | 2010091345 A2 | 8/2010 |
| WO | 2011036053 A1 | 3/2011 |
| WO | 2013043699 A2 | 3/2013 |
| WO | 2013064315 A1 | 5/2013 |
| WO | 2015148063 A1 | 10/2015 |
| WO | 2019125917 A1 | 6/2019 |
| WO | 2019161291 A1 | 8/2019 |

OTHER PUBLICATIONS

Bruschweiler, Dr. H., "Flussigwaschmittel", Tenside Detergents, BASF Corporation (1986) 23, 6 pages.
Crowe, T.G., et al., "Digital Device and Technique for Sensing Distribution of Spray Deposition", American Society of Agricultural Engineers (2005), vol. 48(6), pp. 2085-2093.
Dexter, R.W., "Measurement of Extensional Viscosity of Polymer Solutions and its Effects on Atomization from a Spray Nozzle", Atomization and Sprays, (1996) vol. 6, pp. 167-191.
DOW Personal Care, Kathon CG, "A Safe, Effective, Globally Approved Preservative for Rinse-Off Products", Jun. 2006, 9 pages.
Filipovic-Vincekovic, Dr. N., et al., "Surfactants in Liquid Decontamination Processes", Tenside Surfactants Detergents (1987) 24:3, 6 pages.
Giles, D.K., et al., "Flow Control and Spray Cloud Dynamics From Hydraulic Atomizers", American Society of Agricultural Engineers, (2002) vol. 45(3), pp. 539-546.
Giles, D. Ken, "Independent Control of Liquid Flow Rate and Spray Droplet Size From Hydraulic Atomizers", Atomization and Sprays (1997), vol. 7, pp. 161-181.
Giles, D.K., et al., "Precision Band Spraying with Machine-Vision Guidance and Adjustable Yaw Nozzles", American Society of Agricultural Engineers, (1997) vol. 40(1), pp. 29-36.
Giles, D.K., et al., "Suppression of Aerosol Generation During Spraying and Deposition of Consumer Products", Atomization and Sprays, (2005), vol. 15, pp. 423-438.
Giles, D.K., et al., "Transient Droplet Size Spectra From Trigger Sprayers Dispensing Aqueous Solutions", American Society of Agricultural Engineers, (2005), vol. 48(1), pp. 63-72.
Jadidi, Nazanin, et al., "Synergism and Performance Optimization in Liquid Detergents Containing Binary Mixtures of Anionic-Nonionic, and Anionic-Cationic Surfactants", J. Surfact. Deterg., (2013), 16, pp. 115-121.
Malihi, F.B., et al., "Evaluation of Physico-Chemical Interactions between Linear Alkylbenzene Sulfonate (LAS) and Alcohol Ethoxylates", Physical Chemistry, Tenside Surf. Det. (2011), 48, 5, pp. 395-399.
Raney, Kirk H., "Optimization of Nonionic/Anionic Surfactant Blends for Enhanced Oily Soil Removal", JAOCS (Jul. 1991), vol. 68, No. 7, pp. 525-531.
Rojvoranun, Sureeporn, et al., "Mechanistic Studies of Particulate Soil Detergency: I. Hydrophobic Soil Removal", J. Surfact. Deterg. (2012) 15, pp. 277-289.
Rojvoranun, Sureeporn, et al., "Mechanistic Studies of Particulate Soil Detergency: II. Hydrophobic Soil Removal", J. Surfact. Deterg. (2012) 15, pp. 663-677.
Zoid, T. Ahmed, et al., "Response Surface Methodology as an Approach to the Optimization of a Dishwashing Detergent", Tenside Surf. Det. (2007) 44:2, pp. 94-101.
"The International Search Report and Written Opinion of the International Searching Authority", in connection to PCT/US2018/020424 filed Mar. 1, 2018 dated Jun. 26, 2018.
Ecolab USA Inc., PCT/US2017/033936 filed May 23, 2017, "Notification of Transmittal of the International Search Report and the Written Opinion of the International Searching Authority, or the Declaration", dated Jul. 28, 2017.

* cited by examiner

REDUCED INHALATION HAZARD SANITIZERS AND DISINFECTANTS VIA HIGH MOLECULAR WEIGHT POLYMERS

CROSS-REFERENCE TO RELATED APPLICATIONS

This application claims priority under 35 U.S.C. § 119 to provisional application U.S. Ser. No. 62/465,483, filed Mar. 1, 2017, which is herein incorporated by reference in its entirety.

FIELD OF THE INVENTION

The present invention relates to the field of aqueous compositions for cleaning, sanitizing, and disinfecting. In some embodiments, an antimicrobial quaternary ammonium compound is provided in combination with a polymer component provide a composition having reduced inhalation risk coupled with the sanitizing, disinfectant and/or antimicrobial properties. In other aspects, an antimicrobial quaternary ammonium compound is provided in combination with a surfactant component, a polymer component, and additional functional ingredients. In particular, the combination provides heightened antimicrobial activity and reduced inhalation risk as compared to either the surfactant or the quaternary ammonium compound alone. Beneficially, according to the invention the cleaning composition is provided according to a particular application of use.

BACKGROUND OF THE INVENTION

Antimicrobial agents are chemical compositions that are used to prevent microbiological contamination and deterioration of products, materials, mediums (such as water process streams) and systems. Antimicrobial agents and compositions are used, for example, as disinfectants or sanitizers in association with hard surface cleaning, food preparation, animal feed, cooling water, hospitality services, hospital and medical uses, pulp and paper manufacturing, cleaning textiles, and water processing. Of the diverse categories of antimicrobial agents and compositions, quaternary ammonium compounds represent one of the largest of the classes of agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. However, at high concentrations, generally greater than about 2 to 3 wt. %, they demonstrate acute toxicity. According to the United States Environmental Protection Agency, contact with quaternary ammonium compounds cause contact dermatitis and nasal irritation. Further, certain quaternary ammonium compounds are respiratory sensitizers and are associated with asthma and other respiratory conditions. Personal protection and proper ventilation are required in handling and use of quaternary ammonium compounds in order to limit the inhalation amount. Per the United States Environmental Protection Agency Health Effects Test Guidelines, OPPTS 870.1300 for Acute Inhalation Toxicity, during the development of a generating system for such compositions, particle size analysis should be performed to establish the stability of aerosol concentrations. The mass median aerodynamic diameter particle size should be between 1-4 micrometers. The particle size of hydgroscopic materials should be small enough when dry to assure that the size of the swollen particle will still be within the 1-4 micrometer range.

Further, spray devices create a spray pattern of the composition that contacts the target hard surface. The majority of the composition comes to reside on the target surface, while a small portion of the sprayable composition may become an airborne aerosol or mist consisting of small particles (e.g. an airborne mist or finely divided aerosol) of the cleaning composition that can remain suspended or dispersed in the atmosphere surrounding the dispersal site for a period of time, such as between about 5 seconds to about 10 minutes. Such airborne mist or finely divided aerosol generated during the spraying process can present a substantial problem Such aqueous compositions having a strong base cleaning component in the form of a finely divided aerosol or mist can cause respiratory distress in a user. To alleviate the respiratory distress, some sprayable aqueous compositions have been formulated with reduced quantities of the alkaline cleaning components. Strong caustic has been replaced by reduced alkalinity bases such as bicarbonate or by solvent materials. However, the reduction in concentration or substitution of these materials can often reduce the cleaning activity and effectiveness of the material when used. This necessitates the use of organic surfactants or glycol, alkyl ether or dimethyl sulfoxide solvent materials to enhance the detergent properties of the reduced alkaline materials. Despite improvements seen in sprayable aqueous compositions there remains a need for improved compositions having reduced misting and therefore reduced inhalation, while providing efficacious cleaning, sanitizing and disinfecting.

Development and improvements to polymers for various uses include those disclosed in EP 202,780 disclosing particulate cross-linked copolymers of acrylamide with at least 5 mole percent dialkylaminoalkyl acrylate; U.S. Pat. No. 4,950,725 disclosing the addition of a cross-linking agent both at the beginning, and during the polymerization process under conditions such that its availability for reaction is substantially constant throughout the process; EP 374,458 disclosing water-soluble branched high molecular weight cationic polymers; EP 363,024 disclosing chain transfer agent at the conclusion of polymerization of a DADMAC/ acrylamide copolymer; U.S. Pat. No. 4,913,775 disclosing use of substantially linear cationic polymers such as acrylamide/dimethylaminoethyl acrylate methyl chloride quaternary salt copolymers; U.S. Pat. No. 5,393,381 disclosing branched cationic polyacrylamide powder such as an acrylamide/dimethylaminoethyl acrylate quaternary salt copolymer; and WO2002002662 disclosing water-soluble cationic, anionic, and nonionic polymers, synthesized using water-in-oil emulsion, dispersion, or gel polymerization and having a fast rate of solubilization, higher reduced specific viscosities.

Therefore, it is an object of the invention to reduce inhalation risk of such compositions at high, medium, and low concentrations. Reduced inhalation risk can also be measured indirectly by reduced aerosol mass collection from high volume air sampling. Reduced levels of mass correlate directly to reduced inhalation. This reduction is distinct from a reduction in misting, which is determined from the droplet size of an applied solution, with an increased droplet size indicating reduced misting and atomization. Indeed, an advantage of the liquid compositions of the present invention is that the inhalation risk by the user of said compositions is significantly reduced or diminished. Thus, the compositions herein avoid potential health issues like nose and/or throat irritation and/or coughing or even lung damage, which may otherwise occur from inhalation of quaternary ammonium compounds. A further advantage of the present invention is that also eye irritation and/or damage is prevented when using the cleaning compositions according to the present invention.

Accordingly, it is an objective of the claimed invention to develop an enhanced antimicrobial quaternary ammonium compound-based composition.

It is a further object of the invention is a reduced inhalation product suitable for formulation using polymers in neutral, acidic, and/or or alkaline formulations, including oxidizing formulations.

It is a further object of the invention to provide an effective antimicrobial quaternary ammonium compound-based composition that when in contact with biological matter have a reduced risk of inhalation and exposure.

It is a further object of the invention to provide a synergistic composition of a quaternary ammonium compounds and additional functional ingredients to provide such improvements on acute toxicity levels.

It is an object of the invention to provide an activated composition, having reduced acute toxicity and inhalation risk, having application of use including, for example, hard surface sanitizers, facility sanitizers, water treatment, disinfectant and/or sanitizing surfaces, including high level disinfectants for medical instruments, antimicrobial lubricants, laundry cleaning and sanitizing, antimicrobials having enhanced mildness and reduced irritancy, enhanced combination products, third sink applications, and the like where antimicrobial quaternary ammonium compounds are used.

Other objects, advantages and features of the present invention will become apparent from the following specification taken in conjunction with the accompanying drawings.

BRIEF SUMMARY OF THE INVENTION

The compositions according to the invention provides the ability to maintain equal or enhanced antimicrobial efficacy of quaternary ammonium compounds while simultaneously reducing inhalation risk as a result of incorporation of high molecular weight emulsion and dispersion polymers in the compositions.

In an aspect, a concentrated cleaning composition according to the disclosure comprises a cleaning component comprising a disinfectant, sanitizer, antimicrobial compound, or combinations thereof; and a polymer component, wherein said polymer is a high molecular weight cationic, nonionic, or anionic polymer. According to the disclosure, the cleaning component is a quaternary ammonium compound, an acid sanitizer, an oxidizer, an amine, or combinations thereof; while the polymer component is an inversion emulsion polymer, dispersion polymer, powder polymer, xanthan gum, or combinations thereof.

In an aspect, a cleaning composition according to the disclosure comprises a cleaning component of a quaternary ammonium compound, and a polymer component of a high molecular weight cationic or anionic inversion emulsion polymer; a high molecular weight cationic or anionic dispersion polymer; or a high molecular weight cationic or anionic powder polymer.

In a further aspect, a cleaning composition according to the disclosure comprises a cleaning component of an acid sanitizer, and a polymer component of a high molecular weight cationic, anionic, or nonionic inversion emulsion polymer; a high molecular weight cationic, anionic, or nonionic dispersion polymer; a high molecular weight cationic, anionic, or nonionic powder polymer; or xanthan gum.

In a still further aspect, a cleaning composition according to the disclosure comprises a cleaning component of an oxidizer, and polymer component of a high molecular weight cationic, anionic, or nonionic inversion emulsion polymer; a high molecular weight cationic, anionic, or nonionic dispersion polymer; a high molecular weight cationic, anionic, or nonionic powder polymer; or xanthan gum.

In a still further aspect, a cleaning composition according to the disclosure comprises a cleaning component of an amine, and a polymer component of a high molecular weight cationic, anionic, or nonionic inversion emulsion polymer; a high molecular weight cationic, anionic, or nonionic dispersion polymer; a high molecular weight cationic, anionic, or nonionic powder polymer; or xanthan gum.

The cleaning compositions according to the disclosure may comprise a polymer component with a molecular weight of 1 million Da to 25 million Da; a particular size ranging from 0.1 to 10 microns; and a viscosity of 50 to 5000 cPs. Further, the cleaning compositions may further comprise an acid component, wherein the acid component is present in an amount from about 0.1 wt.-% to about 30 wt.-%, and wherein the acid component provides pH control so that cleaning composition has a pH from 0-6. Still further, the cleaning compositions according to the disclosure may further comprise at least one anionic surfactant, nonionic surfactant, amphoteric surfactant, or combinations thereof, wherein the at least one surfactant is present in an amount from about 0.1 wt.-% to about 30 wt.-%.

The cleaning compositions according to the disclosure may further comprise at least one additional functional ingredient selected from the group consisting of additional surfactants, thickeners and/or viscosity modifiers, solvents, solubility modifiers, humectants, metal protecting agents, stabilizing agents, corrosion inhibitors, sequestrants and/or chelating agents, solidifying agent, sheeting agents, pH modifying components, fragrances and/or dyes, hydrotropes or couplers, buffers, and combinations thereof.

In an aspect of the disclosure, the cleaning compositions provide at least 4 log kill on treated surfaces will providing reduced inhalation risk. Further, the cleaning compositions provide reduced inhalation risk with a median particle size of said composition is about 11 microns or greater.

In a further aspect of the disclosure, a cleaning composition comprises a quaternary ammonium compound having the formula:

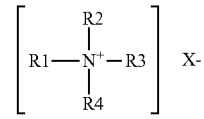

wherein groups R1, R2, R3, and R4 each have less than a C20 chain length, and X— is an anionic counterion; and a polymer component, wherein said polymer component is a high molecular weight cationic or nonionic polymer; wherein the composition is either a ready to use solution or water soluble concentrate and has a pH between about 0 to about 6.

According to an aspect of the disclosure, the quaternary ammonium compound is selected from the group consisting of monoalkyltrimethyl ammonium salts, monoalkyldimethylbenzyl ammonium salts, dialkyldimethyl ammonium salts, heteroaromatic ammonium salts, polysubstituted quaternary ammonium salts, bis-quaternary ammonium salts, polymeric quaternary ammonium salts, and combinations thereof. In a further aspect of the disclosure, the quaternary ammonium compound is present in an amount from about 1 wt.-% to about 50 wt.-%.

In an aspect of the disclosure, the polymer component has a molecular weight of 1 million Da to 25 million Da; a particle size ranging from 0.1 to 10 microns; and a viscosity of 50 to 5000 cPs. Still further, the polymer component is acrylamide, methacrylamide, acrylic acid or its salts, N-t-butyl acrylamide sulfonic acid (ATBS) or its salts, acrylamide tertiary butyl sulfonic acid or its salts, 2-(acryloyloxy)-N,N,N-trimethylethananminium (DMAEA.MCQ), diallyldimethylammonium chloride, dimethylaminoethyl acrylate methyl chloride quaternary salt, acrylamidopropyltrimethylammonium chloride, dimethylaminoethyl methacrylate methyl chloride quaternary salt, methacrylamidopropyltrimethylammonium chloride, or combinations of the same.

In an aspect of the disclosure, the cleaning composition further comprises an acid component, wherein the acid component is present in an amount from about 0.1 wt.-% to about 30 wt.-% and provides pH control so that cleaning composition has a pH from 0-6.

In a further aspect of the disclosure, the cleaning composition further comprises at least one anionic surfactant, nonionic surfactant, amphoteric surfactant or combinations thereof, wherein the at least one surfactant is present in an amount from about 0.1 wt.-% to about 30 wt.-%.

In a still further aspect of the disclosure, the cleaning composition further comprises at least one additional functional ingredient selected from the group consisting of additional surfactants, thickeners and/or viscosity modifiers, solvents, solubility modifiers, humectants, metal protecting agents, stabilizing agents, corrosion inhibitors, sequestrants and/or chelating agents, solidifying agent, sheeting agents, pH modifying components, fragrances and/or dyes, hydrotropes or couplers, buffers, and combinations thereof.

The cleaning compositions according to the disclosure provides at least 4 log kill on treated surfaces while providing reduced inhalation risk. Further, the cleaning compositions according to the disclosure provide reduced inhalation risk with a median particle size of said composition is about 11 microns or greater.

Methods of employing the compositions are also included in the embodiments of the invention. In an aspect of the disclosure, the method of killing microbes comprises applying to a substrate a cleaning composition according to the disclosure, wherein the composition provides at least 4 log kill on treated surfaces while providing a reduced inhalation risk.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENT

The embodiments of this invention are not limited to particular compositions, methods of making and/or methods of employing the same for hard surface sanitizing and disinfecting, including antimicrobial and/or sanitizing application for cleaning compositions, along with alternative cleaning and uses for cleaning compositions, which can vary and are understood by skilled artisans. So that the invention may be more readily understood, certain terms are first defined. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term or abbreviation "AcAm" refers to acrylamide.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the terms "active chlorine", "chlorine", and "hypochlorite" are all used interchangeably and are intended to mean measurable chlorine available in a use solution as evaluated by standard titration techniques known to those of skill in the art. In a preferred aspect, the inverse emulsion polymer compositions provide chlorine-free cleaning compositions.

As used herein, the terms "aerosol" and "mist" refer to airborne dispersions of small particles comprising the cleaning composition that can remain suspended or dispersed in the atmosphere surrounding a cleaning site for at least 5 seconds, more commonly 15 seconds to 10 minutes.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism. For the purpose of this patent application, successful microbial reduction is achieved when the microbial populations are reduced by at least about 50%, or by significantly more than is achieved by a wash with water. Larger reductions in microbial population provide greater levels of protection.

The term or abbreviation "DADMAC" refers to diallyldimethylammonium chloride.

The term or abbreviation "DMAEA" refers to dimethylaminoethyl acrylate.

The term or abbreviation "DMAEM" refers to dimethylaminoethyl methacrylate.

The term or abbreviation "DMAEA BCQ" refers to dimethylaminoethyl acrylate, benzyl chloride quaternary salt.

The term or abbreviation "DMAEA'MCQ" refers to dimethylaminoethyl acrylate, methyl chloride quaternary salt.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). According to this reference a disinfectant should provide a 99.999% reduction (5-log order reduction) within 30 seconds at room temperature, 25±2° C., against several test organisms. According to embodiments of the invention, a disinfecting composition provides a 99.999% reduction (5-log order reduction) of the desired organisms (including bacterial contaminants) at a use temperature. Further, a disinfectant should provide a 99.99% reduction (4-log order reduction) within 30 seconds at room temperature, 25±2° C., against several test organisms. According to embodiments of the invention, a disinfecting composition provides a 99.99% reduction (4-log order reduction) of the desired organisms (including bacterial contaminants) at a use temperature. Further, a disinfectant should provide a 99.9% reduction (3-log order reduction) within 30 seconds at room temperature, 25±2° C., against several test organisms. According to embodiments of the invention, a disinfecting composition provides a 99.9% reduction (3-log order reduction) of the desired organisms (including bacterial contaminants) at a use temperature. As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA. The term or abbreviation "EDTA 4Na+" refers to ethylenediaminetetraacetic acid, tetrasodium salt.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention.

These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, the term "microbe" is synonymous with microorganism. For the purpose of this patent application, successful microbial reduction is achieved when the microbial populations are reduced by at least about 50%, or by significantly more than is achieved by a wash with water. Larger reductions in microbial population provide greater levels of protection. Differentiation of antimicrobial "-cidal" or "-static" activity, the definitions which describe the degree of efficacy, and the official laboratory protocols for measuring this efficacy are considerations for understanding the relevance of antimicrobial agents and compositions. Cleaning compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms. According to embodiments of the invention, a sanitizing composition provides a 99.999% reduction (5-log order reduction) of the desired organisms (including bacterial contaminants) at a use temperature. Further, a sanitizer should provide a 99.99% reduction (4-log order reduction) within 30 seconds at room temperature, 25±2° C., against several test organisms. According to embodiments of the invention, a sanitizing composition provides a 99.99% reduction (4-log order reduction) of the desired organisms (including bacterial contaminants) at a use temperature. Further, a sanitizer should provide a 99.9% reduction (3-log order reduction) within 30 seconds at room temperature, 25±2° C., against several test organisms. According to embodiments of the invention, a sanitizing composition provides a 99.9% reduction (3-log order reduction) of the desired organisms (including bacterial contaminants) at a use temperature. Differentiation of antimicrobial "-cidal" or "-static" activity, the definitions which describe the degree of efficacy, and the official laboratory protocols for measuring this efficacy are considerations for understanding the relevance of antimicrobial agents and compositions. Cleaning compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition The term "surfactant" as used herein is a compound that contains a lipophilic segment and a hydrophilic segment, which when added to water or solvents, reduces the surface tension of the system.

The term "viscosity" is used herein to describe a property of the sprayable aqueous compositions for cleaning, sanitizing and disinfecting according to the invention. As one skilled in the art understands, both dynamic (shear) viscosity and bulk viscosity can be used to describe characteristics of the compositions. The shear viscosity of a liquid describes its resistance to shearing flows. The bulk viscosity of a liquid describes its ability to exhibit a form of internal friction that resists its flow without shear. The measurements of viscosity described herein use the physical until of poise (P) or centipoise (cPs).

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, "weight percent," "wt.-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt.-%," etc.

As used herein, the term "water soluble" refers to a composition or a component if it is at least 90 percent soluble in water, at least 95 percent soluble in water, at least 98 percent soluble in water, at least 99 percent soluble in water, or at least 99.9 percent soluble in water.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Cleaning Compositions

According to the invention, the cleaning compositions comprise of at least one sanitizer, disinfectant, and/or antimicrobial compound and at least one polymer compound and provide cleaning activity with a reduced acute toxicity as a result of reduced inhalation risk of the composition. The present invention relates to reduced-misting and reduced-inhalation aqueous cleaning compositions comprising, consisting of or consisting essentially of at least one sanitizer, disinfectant and/or antimicrobial compound and at least one polymer compound. In some embodiments, the compositions may be dispensed with a trigger sprayer, such as non-low velocity or a low velocity trigger sprayer. The compositions may be dispensed in alternative manners as well. The cleaning compositions provide ease in manufacturing as a result of the rapid dispersion of the polymer into homogenous solutions. The cleaning compositions provide further benefits in addition to the ease in manufacturing, including for example, ease in application when using spray applications due to the reduced viscosity profiles allowing ease of use with spray triggers. Still further, the cleaning compositions provide little to no misting of the formulations and increased rate of cleaning in comparison to compositions comprising conventional thickeners. Further aspects of reduced misting compositions are discussed in U.S. patent application Ser. No. 15/602,532, filed May 23, 2017, now U.S. Pub. No. 2017/0335254; and U.S. patent application Ser. No. 15/603,039, filed May 23, 2017, now U.S. Pub. No. 2017/0335253, each of which is incorporated by reference in its entirety.

The cleaning composition may be referred to as a non-Newtonian fluid. Newtonian fluids have a short relaxation time and have a direct correlation between shear and elongational viscosity (the elongational viscosity of the fluid equals three times the shear viscosity). Shear viscosity is a measure of a fluid's ability to resist the movement of layers relative to each other. Elongational viscosity, which is also known as extensional viscosity, is a measure of a fluid's ability to stretch elastically under elongational stress. Non-Newtonian fluids do not have a direct correlation between shear and elongational viscosity and are able to store elastic energy when under strain, giving exponentially more elongational than shear viscosity and producing an effect of thickening under strain (i.e., shear thickening). These properties of non-Newtonian fluids result in the cleaning composition that has a low viscosity when not under shear but that thickens when under stress from the trigger sprayer forming larger droplets.

In some embodiments, the cleaning composition has a relatively low shear viscosity when not under strain. In an embodiment, the shear viscosity of the cleaning composition containing the inverse emulsion polymer(s) is comparable to the shear viscosity of water and may be referred to as a "thin liquid". A suitable shear viscosity for the cleaning compositions containing a polymer(s) is from about 1 to 1000 cPs, preferably from 1 to 100 cPs. In one example, the anti-mist components do not increase the shear viscosity of the cleaning composition when not under strain and the increased shear viscosity is created by other components, such as a surfactant. The present invention provides an unexpected benefit in the viscosity of the anti-mist compositions as a result of the flexible viscoelastic compositions afforded by the inverse emulsion polymers.

In some embodiments, the median particle size of the dispensed solution of the reduced-misting cleaning compositions is sufficiently large to reduce misting and thereby reduce the inhalation risk associated with high misting compositions. As one skilled in the art appreciates, particles having droplet size of less than about 10 microns can be readily inhaled. Moreover, particles having droplet size of less than about 0.1 microns can be readily inhaled into the lungs. Therefore, in many aspects of the invention the testing and evaluation of the cleaning compositions according to the invention focus on the reduction of misting, in particular reduction or elimination of micron sizes of about 10 or less. In an aspect of the invention, a suitable median particle size is about 11 microns or greater, 50 microns or greater, 70 microns or greater, about 10 microns or greater, about 150 microns or greater, or about 200 microns or greater. The suitable median particle size may depend on the composition of the ready to use composition (RTU). For example, a suitable median particle size for a strongly alkaline or acidic use solution may be about 100 microns or greater, and more particularly about 150 microns or greater, and more particularly about 200 microns or greater. A suitable median particle size for a moderately alkaline or acidic RTU may be about 11 microns or greater, preferably about 50 microns or greater, and more preferably about 150 microns or greater.

The cleaning compositions according to the invention beneficially provide stable compositions in terms of retained performance of the polymer, solution stability, and microbial efficacy, wherein the polymer retains stability for at least about one year at ambient temperature of about 60° F. to about 80° F., or at least about two years at ambient temperature of about 60° F. to about 80° F. The stability is measured by the maintained anti-misting properties of the cleaning compositions.

In an aspect, the cleaning compositions according to the invention comprises, consist of, and/or consist essentially of the components as shown in Table 1 wherein the active sanitizer, disinfectant and/or antimicrobial compound employed impacts the selection of the polymer form and charge to provide the unexpected and beneficial effect of having reduced inhalation risk coupled with the sanitizing, disinfectant and/or antimicrobial properties.

TABLE 1

| | Sanitizer, Disinfectant, and/or Antimicrobial Compound | | | |
|---|---|---|---|---|
| | Quaternary Ammonium Compounds | Acid Sanitizers | Oxidizers | Amines |
| Polymer Form | Inverse Emulsion, Dispersion, and/or Powder | Inverse Emulsion, Dispersion, Powder and/or Xanthan Gum | Inverse Emulsion, Dispersion, Powder and/or Xanthan Gum | Inverse Emulsion, Dispersion, Power and/or Xanthan Gum |
| Polymer Charge | Cationic, Nonionic | Cationic, Nonionic, Anionic | Cationic, Nonionic, Anionic | Cationic, Nonionic, Anionic |

Cleaning Component

The cleaning compositions according to the invention contain a cleaning compound which comprises at least one sanitizer, disinfectant, or antimicrobial compound. In an embodiment of the invention, the cleaning compound is a quaternary ammonium compound, an acid sanitizer, an oxidizer, an amine, or combinations thereof.

Quaternary Ammonium Compounds

According to an embodiment of the invention, the cleaning compositions comprise at least one quaternary ammonium compound and at least one polymer compound. Without wishing to be limited to a particular theory of the invention, the cleaning compositions of the present invention, when utilized at acidic pH, influence the interactions between quaternary ammonium compounds and protein. In particular, the utilization of quaternary ammonium compounds at an acidic pH reduces electrostatic interactions between positively charged quaternary ammonium compounds with negatively or partially negatively charged biological matter reduces the risk of toxicity and the inhalation risks associated with quaternary ammonium compounds. Further, the addition of the polymer component causes the composition to resist formulation of an amount of mist or aerosol during storage and application that can cause respiratory distress.

The cleaning compositions according to the invention overcome the concerns of acute toxicity of quaternary ammonium compounds while providing efficacious antimicrobial and/or sanitizing capabilities. The compositions of quaternary ammonium compound and acid component reduce acute toxicity. Without seeking to be bound to a particular theory, control of the pH of concentrated compositions containing quaternary ammonium compounds reduces electrostatic interactions between quaternary ammonium compounds and biological matter, specifically during inhalation. Theoretical surface charge of casein proteins as a function of pH are summarized in Table 2, to illustrate pH-electrostatic charge relationship of proteins. i.e., biological matter. As shown in Table 2 and as one of ordinary skill in the art would appreciate, as the pH nears the isoelectric point, a protein while demonstrate a net zero charge.

TABLE 2

| pH | Protein Net Charge | Theoretical Compatibility with Cationic Surfactants |
|---|---|---|
| 0-4.59 | Net cationic | Positive (MW, charge, molar ratio dependent) |
| 4.6 | Net zero charge | Neutral (MW, charge, molar ratio dependent) |
| 4.61-12 | Net anionic | Negative interactions (MW, charge, molar ratio dependent) |

At physiological pH of the lungs, about 7.25-7.45, most biological matter has an anionic change. If the biological matter is then less anionic, i.e., close to/at/or below its respective isoelectric point or pKa, it is believed that according to the theoretical compatibility shown in Table 2, quaternary ammonium compounds and biological matter have reduced electrostatic interactions.

In an aspect of the invention where a surfactant is included in the cleaning compositions, cationic surfactants are disfavored due to an increase in electrostatic interactions, thus increasing the toxicity of the compositions.

As such, anionic, nonionic, and amphoteric surfactants, and combinations thereof are favored in order to decrease interactions between biological matter and quaternary ammonium compounds. Similarly, acid components are selected in order to control pH as well as aid in the decrease of electrostatic interactions. Further discussion of quaternary ammonium compounds and their suitable for use in an reduced inhalation cleaning composition can be found in U.S. patent application Ser. No. 15/445,146, filed Feb. 28, 2017 [attorney docket number PT10767USU1], the entire contents of which are incorporated herein by reference in its entirety.

The cleaning compositions according to an embodiment of the invention include at least one quaternary ammonium compound. Certain quaternary ammonium compounds are known to have antimicrobial activity. Accordingly, various quaternary ammonium compound with antimicrobial activity can be used in the composition of the invention. In an aspect, the quaternary ammonium compound is an antimicrobial "quat." The term "quaternary ammonium compound" or "quat" generally refers to any composition with the formula 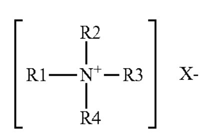 where R1-R4 are alkyl groups that may be alike or different, substituted or unsubstituted, saturated or unsaturated, branched or unbranched, and cyclic or acyclic and may contain ether, ester, or amide linkages; they may be aromatic or substituted aromatic groups. In an aspect, groups R1, R2, R3, and R4 each have less than a C20 chain length. X— is an anionic counterion. The term "anionic counterion" includes any ion that can form a salt with quaternary ammonium. Examples of suitable counterions include halides such as chlorides and bromides, propionates, methosulphates, saccharinates, ethosulphates, hydroxides, acetates, phosphates, carbonates (such as commercially available as Carboquat H, from Lonza), and nitrates. Preferably, the anionic counterion is chloride.

In some embodiments, quaternary ammoniums having carbon chains of less than 20 are included in compositions of the invention. Examples of quaternary ammonium compounds useful in the present invention include but are not limited to alkyl dimethyl benzyl ammonium chloride, alkyl dimethyl ethylbenzyl ammonium chloride, octyl decyl dimethyl ammonium chloride, dioctyl dimethyl ammonium chloride, and didecyl dimethyl ammonium chloride to name a few. A single quaternary ammonium or a combination of more than one quaternary ammonium may be included in compositions of the invention. Further examples of quaternary ammonium compounds useful in the present invention include but are not limited to benzethonium chloride, ethyl benzethonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), and denatonium.

In some embodiments, quaternary ammoniums having carbon chains of less than 20 or C2-C20 are included in compositions of the invention. In other embodiments, quaternary ammoniums having carbon chains of C6-C18, C12-C18, C12-C16 and C6-C10 are included in compositions of the invention. Examples of quaternary ammonium compounds useful in the present invention include but are not limited to alkyl dimethyl benzyl ammonium chloride, alkyl dimethyl ethylbenzyl ammonium chloride, octyl decyl dimethyl ammonium chloride, dioctyl dimethyl ammonium chloride, and didecyl dimethyl ammonium chloride to name a few. A single quaternary ammonium or a combination of more than one quaternary ammonium may be included in compositions of the invention.

Further examples of quaternary ammonium compounds useful in the present invention include but are not limited to benzethonium chloride, ethylbenzyl alkonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), denatonium, and mixtures thereof. In an aspect, combinations of quaternary ammonium compounds are particularly preferred for compositions of the invention, such as for example the commercially-available products Bardac 205/208M.

In some embodiments depending on the nature of the R group, the anion, and the number of quaternary nitrogen atoms present, the antimicrobial quaternary ammonium compounds may be classified into one of the following categories: monoalkyltrimethyl ammonium salts; monoalkyldimethylbenzyl ammonium salts; dialkyldimethyl ammonium salts; heteroaromatic ammonium salts; polysubstituted quaternary ammonium salts; bis-quaternary ammonium salts; and polymeric quaternary ammonium salts. Each category will be discussed herein.

Monoalkyltrimethyl ammonium salts contain one R group that is a long-chain alkyl group, and the remaining R groups are short-chain alkyl groups, such as methyl or ethyl groups. Some non-limiting examples of monoalkyltrimethyl ammonium salts include cetyltrimethylammonium bromide, commercial available under the tradenames Rhodaquat M242C/29 and Dehyquart A; alkyltrimethyl ammonium chloride, commercially available as Arquad 16; alkylaryltrimethyl ammonium chloride; and cetyldimethyl ethylammonium bromide, commercially available as Ammonyx DME.

Monoalkyldimethylbenzyl ammonium salts contain one R group that is a long-chain alkyl group, a second R group that is a benzyl radical, and the two remaining R groups are short-chain alkyl groups, such as methyl or ethyl groups. Monoalkyldimethylbenzyl ammonium salts are generally compatible with nonionic surfactants, detergent builders, perfumes, and other ingredients. Some non-limiting examples of monoalkyldimethylbenzyl ammonium salts include alkyldimethylbenzyl ammonium chlorides, commercially available as Barquat from Lonza Inc.; and benzethonium chloride, commercially available as Lonzagard, from Lonza Inc. Additionally, the monoalkyldimethylbenzyl ammonium salts may be substituted. Non-limiting examples of such salts include dodecyldimethyl-3,4-dichlorobenzyl ammonium chloride. Finally, there are mixtures of alkyldimethylbenzyl and alkyldimethyl substituted benzyl (ethylbenzyl) ammonium chlorides commercially available as BTC 2125M from Stepan Company, and Barquat 4250 from Lonza Inc.

Dialkyldimethyl ammonium salts contain two R groups that are long-chain alkyl groups, and the remaining R groups are short-chain alkyl groups, such as methyl groups. Some non-limiting examples of dialkyldimethyl ammonium salts include didecyldimethyl ammonium halides, commercially available as Bardac 22 from Lonza Inc.; didecyl dimethyl ammonium chloride commercially available as Bardac 2250 from Lonza Inc.; dioctyl dimethyl ammonium chloride, commercially available as Bardac LF and Bardac LF-80 from Lonza Inc.); and octyl decyl dimethyl ammonium chloride sold as a mixture with didecyl and dioctyl dimethyl ammonium chlorides, commercially available as Bardac2050 and 2080 from Lonza Inc.

Heteroaromatic ammonium salts contain one R group that is a long-chain alkyl group, and the remaining R groups are provided by some aromatic system. Accordingly, the quaternary nitrogen to which the R groups are attached is part of an aromatic system such as pyridine, quinoline, or isoquinoline. Some non-limiting examples of heteroaromatic ammonium salts include cetylpyridinium halide, commercially available as Sumquat 6060/CPC from Zeeland Chemical Inc.; 1-[3-chloroalkyl]-3,5,7-triaza-1-azoniaadamantane, commercially available as Dowicil 200 from The Dow Chemical Company; and alkyl-isoquinolinium bromide.

Polysubstituted quaternary ammonium salts are a monoalkyltrimethyl ammonium salt, monoalkyldimethylbenzyl ammonium salt, dialkyldimethyl ammonium salt, or heteroaromatic ammonium salt wherein the anion portion of the molecule is a large, high-molecular weight (MW) organic ion. Some non-limiting examples of polysubstituted quaternary ammonium salts include alkyldimethyl benzyl ammonium saccharinate, and dimethylethylbenzyl ammonium cyclohexylsulfamate.

Bis-quaternary ammonium salts contain two symmetric quaternary ammonium moieties having the general formula:

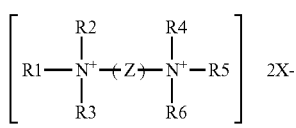

Where the R groups may be long or short chain alkyl, a benzyl radical or provided by an aromatic system. Z is a carbon-hydrogen chain attached to each quaternary nitrogen. Some non-limiting examples of bis-quaternary ammonium salts include 1,10-bis(2-methyl-4-aminoquinolinium chloride)-decane; and 1,6-bis[1-methyl-3-(2,2,6-trimethyl cyclohexyl)-propyldimethylammonium chloride] hexane or triclobisonium chloride.

In an aspect, the quaternary ammonium compound is a medium to long chain alkyl R group, such as from 8 carbons to about 20 carbons, from 8 carbons to about 18 carbons, from about 10 to about 18 carbons, and from about 12 to about 16 carbons, and providing a soluble and good antimicrobial agent.

In an aspect, the quaternary ammonium compound is a short di-alkyl chain quaternary ammonium compound having an R group, such as from 2 carbons to about 12 carbons, from 3 carbons to about 12 carbons, or from 6 carbons to about 12 carbons.

In a preferred aspect, the quaternary ammonium compound is an alkyl benzyl ammonium chloride, a dialkyl benzyl ammonium chloride, a blend of alkyl benzyl ammonium chloride and dialkyl benzyl ammonium chloride, didecyl dimethyl ammonium chloride, dioctyl dimethyl ammonium chloride, a blend of didecyl dimethyl ammonium chloride and dioctyl dimethyl ammonium chloride, or mixtures thereof. In a preferred embodiment, the quaternary ammonium compound used in the cleaning compositions of the invention is comprised of a mixture of dialkyl quaternary ammonium and alkyl benzyl quaternary ammonium.

According to embodiments of the invention providing cleaning compositions, an effective amount of the quaternary ammonium compound is provided in combination with a polymer to provide antimicrobial efficacy against a broad spectrum of microbes, including gram negative microbes such as *E. coli*. Suitable concentrations of the quaternary ammonium compound in such a use solution include at least about 10 ppm, at least about 50 ppm, or at least about 100 ppm, or at least about 150 ppm, or at least about 200 ppm, or at least about 250 ppm, or at least about 300 ppm, or from about 100-500 ppm, or from about 100-300 ppm, or any ranges therein. In some aspects, the activated microbial compositions according to the invention provide efficacy against gram negative conventionally requirement more than 150 ppm quaternary ammonium compounds for any antimicrobial efficacy at concentrations below about 150 ppm, or below about 100 ppm according to the synergy in combination with the anionic surfactants and/or acids. Without being limited according to the invention, all ranges recited are inclusive of the numbers defining the range and include each integer within the defined range.

Additional suitable concentrations of the quaternary ammonium compound in a use solution for the cleaning compositions include between about 1 ppm and about 10,000 ppm, 1 ppm and about 1,000 ppm, 5 ppm and about 400 ppm, 10 ppm and about 400 ppm, 20 ppm and about 400 ppm, 25 ppm and about 400 ppm, 50 ppm and about 400 ppm, 75 ppm and about 400 ppm, or 100 ppm and about 400 ppm. Additional suitable concentrations of the quaternary ammonium compound in a use solution for the cleaning compositions include between about 0.0001 wt.-% to about 10 wt.-%, about 0.001 wt.-% and about 10 wt.-%, about 0.01 wt.-% and about 10 wt.-%, about 1.0 wt.-% to and about 10 wt.-%. Without being limited according to the invention, all ranges recited are inclusive of the numbers defining the range and include each integer within the defined range.

Acid Sanitizers

Various acid sanitizers can be employed according to the invention. In embodiments of the invention, the acid sanitizer may be a carboxylic acid, peracid, mineral acid, organic acid, amino acid, fatty acid, linear alkylbenzene. It is to be understood that derivatives of each and combinations of acid sanitizers may be employed by the present invention.

In an aspect of the invention, the acid sanitizer is a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxyl groups. Carboxylic acids have a tendency to acidify aqueous compositions in which they are present as the hydrogen atom of the carboxyl group is active and may appear as an anion. The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH. Examples of such carboxylic acids include, but are not limited to, acetic acid, citric acid, succinic acid, adipic acid, hydroxyacetic acid, and lactic acid. One of skill in the art will appreciate that other carboxylic acids may be used for purposes of the invention.

A variety of C6-C18 peroxyacids may be employed in the composition of the invention such as peroxyfatty acids, monoperoxy- or diperoxydicarboxylic acids, and peroxyaromatic acids. The C6-C18 peroxyacids employed in the present invention may be structurally represented as follows: R1-CO3 H, wherein R1 is a hydrocarbon moiety having from about 5 to 17 carbon atoms (a C18 peroxyacid is generally represented structurally as C7-CO3 H). R1 may have substituents in the chain, e.g., —OH, CO2 H, or heteroatoms (e.g., —O— as in alkylether carboxylic acids), as long as the antimicrobial properties of the overall composition are not significantly affected. It should be recognized that "R1" substituents or heteroatoms may change the overall acidity (i.e., pKa) of the carboxylic acids herein described. Such modification is within the contemplation of the present invention provided the advantageous antimicrobial performance is maintained. Furthermore, R1 may be linear, branched, cyclic or aromatic. Preferred hydrocarbon moieties (i.e. preferred R1's) include linear, saturated, hydrocarbon aliphatic moieties having from 7 to 11 carbon atoms (or 8 to 12 carbon atoms per molecule).

Specific examples of suitable C6-C18 carboxylic fatty acids which can be reacted with hydrogen peroxide to form peroxyfatty acids include such saturated fatty acids as hexanoic (C6), enanthic (heptanoic) (C7), caprylic (octanoic) (C8), pelargonic (nonanoic) (C9), capric (decanoic) (C10), undecyclic (undecanoic) (C11), lauric (dodecanoic) (C12), trideclic (tridecanoic) (C13), myristic (tetradecanoic) (C14), palmitic (hexadecanoic) (C16), and stearic (octodecanoic) (C18). These acids can be derived from both natural and synthetic sources. Natural sources include animal and vegetable fats or oils which should be fully hydrogenated. Synthetic acids can be produced by the oxidation of petroleum wax. Particularly preferred peroxyfatty acids for use in the composition of the invention are linear monoperoxy aliphatic fatty acids such as peroxyoctanoic acid, peroxydecanoic acid, or mixtures thereof.

Other suitable C6-C18 peroxyacids are derived from the oxidation of dicarboxylic acids and aromatic acids. Suitable dicarboxylic acids include adipic acid (C6) and sebacic acid (C10). An example of a suitable aromatic acid is benzoic acid. These acids can be reacted with hydrogen peroxide to form the peracid form suitable for use in the composition of the invention. Preferred peracids in this group include monoperoxy- or diperoxyadipic acid, monoperoxy- or diperoxysebacic acid, and peroxybenzoic acid.

The above peroxyacids provide antibacterial activity against a wide variety of microorganisms, such as gram positive (e.g., *Staphylococcus aureus*) and gram negative (e.g., *Escherichia coli*) microorganisms, yeast, molds, bacterial spores, etc. When the above C6-C18 peroxyacids are combined with a C1-C4 peroxycarboxylic acid, greatly enhanced activity is shown compared to the C1-C4 peroxycarboxylic acid alone or the C6-C18 peroxyacid alone. The C1-C4 peroxycarboxylic acid component can be derived from a C1-C4 carboxylic acid or dicarboxylic acid by reacting the acid with hydrogen peroxide. Examples of suitable C1-C4 carboxylic acids include acetic acid, propionic acid, glycolic acid, and succinic acid. Preferable C1-C4 peroxycarboxylic acids for use in the composition of the invention include peroxyacetic acid, peroxypropionic acid, peroxyglycolic acid, peroxysuccinic acid, or mixtures thereof.

The peracid components used in the composition of the invention can be produced in a simple manner by mixing a hydrogen peroxide (H2O2) solution with the desired amount of acid. With the higher molecular weight fatty acids, a hydrotrope coupler may be required to help solubilize the fatty acid. The H2O2 solution also can be added to previously made peracids such as peracetic acid or various perfatty acids to produce the peracid composition of the invention. The concentrate can contain about 1 to 50 wt. %, preferably about 5 to 25 wt. % of hydrogen peroxide. U.S. Pat. No. 5,200,189, filed Jul. 31, 1991 further discloses the use of peracids in cleaning compositions and is hereby incorporated by reference in its entirety.

In an aspect of the invention, the acid sanitizer is a mineral acid, i.e., an inorganic acid. Examples of such mineral acids include, but are not limited to, phosphoric acid, sulfamic acid, sulfuric acid, nitric acid, and hydrocholoric acid. Generally, all mineral acids form hydrogen ions and the conjugate base ions when dissolved in water. For example, sulfuric acid forms hydrogen sulfate in aqueous solutions via complete ionization to form hydronium ions and hydrogen sulfate. Such conjugate bases are also useful acid components for purposes of the invention.

In an aspect of the invention, the acid sanitizer is an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof.

In an aspect of the invention, the acid sanitizer is an amino acid and/or an amino acid derivative. Generally, an amino acid contains an amine functional group and a carboxylic acid functional group, usually along with a side chain group to each amino acid. Suitable amino acid and/or amino acid derivatives include, but are not limited to alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, selenocysteine, pyrrolysine, and derivatives thereof.

In an aspect of the invention, the acid sanitizer is a fatty acid and/or fatty acid surfactant. Antimicrobially active acids have been used in sanitizing operations. For instance, U.S. Pat. No 404,040 describes a sanitizing composition comprising aliphatic, short chain fatty acids, a hydrotrope or solubilizer for the fatty acids, and a hydrotrope-compatible acid, and U.S. Pat. No. 5,330,769 describes fatty acid sanitizer concentrates and diluted final solutions which include individual amounts of germicidally effective fatty acid, hydrotrope, a strong acid group consisting of phosphoric acid and sulfuric acid or mixtures thereof sufficient to lower the pH of the final solutions to about 1-5, and a concentrate stabilizing weak acid component selected from the group consisting of propionic, butyric and valeric acids and mixtures thereof. As used herein, the term "fatty acid" includes any of a group of carboxylic acids that include an alkyl chain. In some embodiments, the alkyl groups can be linear or branched, and saturated or unsaturated. The chain of alkyl groups contains any length of carbon atoms. In some embodiments, the chain of alkyl groups contains from 4 to 12 carbon atoms, 5 to 11 carbon atoms, or 8 to 10 carbon atoms. Exemplary fatty acids can be selected from hexanoic acid, heptanoic acid, octanoic acid, nonanoic acid, decanoic acid, lauric acid, palmitic acid, stearic acid, oleic acid, caproic acid, caprylic acid, capric acid and mixtures thereof. Exemplary longer alkyl chain fatty acids can be selected from for example myristic acid, arachidic acid, behenic acid, lignoceric acid, cerotic acid, myristoleic acid, palmitoleic acid, sapienic acid, elaidic acid, vaccenic acid, linoleic acid, linoelaidic acid, a-linolenic acid, arachidonic acid, eicosapentaenoic acid, erucic acid, decosahexaenoic acid, gadoleic acid, erucic acid, margaric acid, behenic acid, ricinoleic acid, lignoceric acid, licanic acid, eleostearic acid and mixtures thereof.

In an aspect of the invention, the acid sanitizer is a linear alkylbenzene. Suitable linear alkylbenzenes include linear alkylbenzene sulfonate (LAS) and Linear alkylbenzene sulfonic acid (LABSA). Others which can be employed are alkyl benzene sulfonates, alkyl sulfonates, alkyl ether sulfates, alpha olefin sulfonates, alkyl sarcosinates, and mixtures thereof.

Oxidizers

According to an embodiment of the invention, the cleaning compositions comprise at least one oxidizer and at least one polymer compound. The oxidizer can be any oxidizer that is compatible with a cationic, nonionic, and/or anionic polymers. Examples of such oxidizers include nonorganic oxidizing substances such as, hydrogen peroxide, sodium percarbonate, sodium periodate, sodium persulfate, ammonium persulfate, sodium perborate, sodium peroxide, calcium peroxide, silver (II) oxide, ozone, and chlorine dioxide. The oxidizers also include organic oxidizing substance for example, diacyl peroxides, such as benzoyl peroxide, ketone peroxides, such as 2,4-pertanedione peroxide, peroxydicarbonates, such as diisopropyl peroxydicarbonate, peroxyesters, such as t-butylperoxy maleic acid, dialkyl peroxides, such as dicumyl peroxide, hydroperoxyides, such as t-butyl hydroperoxide, and peroxyketals, such as 2,2-di(t-butyl peroxy) butane. Additional oxidizers are disclosed in U.S. Pat. No. 5,616,616, filed Jun. 1, 1994 and is hereby incorporated by reference in its entirety.

Amines

The cleaning component may also be an antimicrobial amine. The amine may be a primary, secondary, or tertiary amine. Alternatively, the composition can include a quaternary ammonium compound. The amine concentration in the system can range from about 0.5 to about 8.5 wt. %, about 1.0 to about 3.0 wt. %, or about 1.25 to about 2.0 wt. %. The amine is preferably a tertiary amine. But, other exemplary antimicrobial amines are: aliphatic amines; aliphatic amine salts such as: aliphatic ammonium salts; ether amines such as: those commercially available from Tomah Products as PA-19, PA-1618, PA-1816, DA-18, DA-19, DA-1618, DA-1816; or ether amines with the formulas $R_1$—O—$R_2$—$NH_2$, $R_1$—O—$R_2$—NH—$R_3$—$NH_2$, or mixtures thereof, where (independently): $R_1$=a linear saturated or unsaturated C6-C18 alkyl, $R_2$=a linear or branched C1-C8 alkyl, and $R_3$=a linear or branched C1-C8 alkyl, or $R_1$=a linear C12-C16 alkyl, $R_2$=a C2-C6 linear or branched alkyl; and $R_3$=a C2-C6 linear or branched alkyl, or $R_1$=a linear alkyl C12-C16, or a mixture of linear alkyl C10-C12 and C14-C16 $R_2$=C3, and $R_3$=C3; ether amine salts such as: ether ammonium salts; diamines such as: N-coco-1,3-propylene diamine (such as Duomeen®-Akzo Chemie America, Armak Chemicals); N-oleyl-1,3-propylene diamine (such as Duomeen®-Akzo Chemie America, Armak Chemicals); N-tallow-1,3-propylene diamine (such as Duomeen® Akzo Chemie America, Armak Chemicals); diamine salts such as: diamine acetate (or other counterion), or diamine sales with the formulas $[(R_1)NH(R_2)NH_3]^+(CH_3COO)^-$ or $[(R_1)NH_2(R_2)NH_3^+](CH_3COO)_2$— where: $R_1$=a C10-C18 aliphatic group or an ether group having the formula $R_{10}OR_{11}$ where $R_{10}$=a C10-C18 aliphatic group and $R_{11}$=a C1-C5 alkyl group; and $R_2$=a C1-C5 alkylene group, or $R_1$=a C10-C18 aliphatic group derived from a fatty acid, and R2=propylene. Further suitable amines are disclosed in U.S. Pat. No. 7,964,548, filed Apr. 5, 2010 and is hereby incorporated by reference in its entirety.

Polymer Component

The cleaning compositions according to the invention include a polymer component. As shown in Table 1, the selection of the cleaning component influences the desired charge of the polymer in order to achieve the desired reduced inhalation risk while beneficially providing the cleaning, sanitizing, disinfecting and/or antimicrobial efficacy. In an aspect of the invention, the polymer may have a cationic, nonionic, or anionic charge and may come in the form of an inverse emulsion polymer, dispersion polymer, powder polymer, and/or xanthan gum.

Inverse Emulsion Polymer

The cleaning compositions according to an embodiment of the invention include an inverse emulsion polymer. In an aspect, the inverse emulsion polymer is a water-soluble modified polymer. In an aspect, the inverse emulsion polymer may be cationic, anionic, nonionic, amphoteric and/or associative. The terms emulsion polymer and latex polymer may be used interchangeably herein, referring to a water-in-oil (W/O) emulsion polymer comprising a cationic, anionic, nonionic, and/or zwitterionic polymer.

In an aspect, the inverse emulsion polymer has a high molecular weight of from about 3,000 Da to about 50 million Da, from about 500,000 Da to about 30 million Da, from about 1 million Da to about 25 million Da, and preferably from about 3 million Da to about 20 million Da.

In an aspect, the inverse emulsion polymer has an intrinsic viscosity above about 1, more preferably above about 6 and still more preferably from about 15 to about 30 dl/g. The reduced specific viscosity of the inverse emulsion polymer is generally above 3, preferably above about 8 and frequently above about 24 dl/g.

In an aspect, the inverse emulsion polymers according to the invention have a particle size ranging from about 0.1 to about 10 microns, preferably from about 0.25 to about 3 microns.

In an aspect, the inverse emulsion polymers according to the invention have a bulk viscosity of ranging from about 50-5000 cPs, and preferably from about 100-2000 cPs.

The inverse emulsion polymers according to the invention are stabilized dispersions of flexible polymer chains containing aqueous droplets in an inert hydrophobic phase. In an aspect, the inverse emulsion polymers are comprised of three components including (1) a hydrophobic or hydrocarbon continuous oil phase, (2) an aqueous phase, and (3) a water-in-oil emulsifying agent (i.e. surfactant system). In an aspect, the inverse emulsion polymers are hydrocarbon continuous with the water-soluble polymers dispersed within the hydrocarbon matrix. The inverse emulsion polymers are then "inverted" or activated for use by releasing the polymer from the particles using shear, dilution, and, generally, another surfactant. See U.S. Pat. No. 3,734,873 which is incorporated herein by reference. Representative preparations of high molecular weight inverse emulsion polymers are described in U.S. Pat. Nos. 2,982,749; 3,284,393, and 3,734,873, each of which are incorporated herein by reference.

In another aspect, an inverse emulsion polymer is formed through the polymerization of an aqueous solution of monomers under free radical polymerization conditions to form a polymer solution, as disclosed in U.S. Pat. Nos. 6,605,674 and 6,753,388, each of which are incorporated herein by reference. In a preferred aspect, the inverse emulsion polymer is obtained by polymerizing an aqueous solution of ethylenically unsaturated water-soluble or water-dispersible monomers and/or comonomers emulsified in a hydrophobic continuous phase by using oil- and/or water soluble initiators via radical polymerization.

As used herein, the term "monomer" for an inverse emulsion polymer means a polymerizable allylic, vinylic or acrylic compound. The monomer may be anionic, cationic, nonionic and/or zwitterionic. In some embodiments vinyl monomers are preferred, and in other embodiments acrylic and/or acrylamide monomers, such as acrylic acid or its salts, N-t-butyl acrylamide sulfonic acid (ATBS) or its salts, acrylamide tertiary butyl sulfonic acid or its salts, and 2-(acryloyloxy)-N,N,N-trimethylethananminium (DMAEA.MCQ), are more preferred.

In an embodiment, nonionic monomers are particularly suitable for use in neutral, acidic, alkaline and/or oxidizing cleaning compositions. Representative nonionic, water-soluble monomers include acrylamide, methacrylamide, N,N-dimethylacrylamide, N,N-diethylacrylamide, N-isopropylacrylamide, N-vinylformamide, N-vinylmethylacetamide, N-vinyl pyrrolidone, hydroxyethyl methacrylate, hydroxyethyl acrylate, hydroxypropyl acrylate, hydroxypropyl methacrylate, N-tert-butylacrylamide, N-methylolacrylamide, and the like.

In an embodiment, anionic monomers are particularly suitable for use in alkaline, neutral and/or oxidizing cleaning compositions. Representative anionic monomers include acrylic acid, and its salts, including, but not limited to sodium acrylate, and ammonium acrylate, methacrylic acid, and its salts, including, but not limited to sodium methacrylate, and ammonium methacrylate, 2-acrylamido-2-methylpropanesulfonic acid (ATBS), the sodium salt of ATBS, acrylamide tertiary butyl sulfonic acid or its salts, sodium vinyl sulfonate, styrene sulfonate, maleic acid, and its salts, including, but not limited to the sodium salt, and ammonium salt, sulfonate itaconate, sulfopropyl acrylate or methacrylate or other water-soluble forms of these or other polymerizable carboxylic or sulphonic acids. Sulfomethylated acrylamide, allyl sulfonate, sodium vinyl sulfonate, itaconic acid, acrylamidomethylbutanoic acid, fumaric acid, vinylphosphonic acid, vinylsulfonic acid, allylphosphonic acid, sulfomethylated acrylamide, phosphonomethylated acrylamide, and the like.

In an embodiment, cationic monomers are particularly suitable for use in acidic and/or oxidizing cleaning compositions. Representative cationic monomers include dialkylaminoalkyl acrylates and methacrylates and their quaternary or acid salts, including, but not limited to, dimethylaminoethyl acrylate methyl chloride quaternary salt, dimethylaminoethyl acrylate methyl sulfate quaternary salt, dimethylaminoethyl acrylate benzyl chloride quaternary salt, dimethylaminoethyl acrylate sulfuric acid salt, dimethylaminoethyl acrylate hydrochloric acid salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, dialkylaminoalkylacrylamides or methacrylamides and their quaternary or acid salts such as acrylamidopropyltrimethylammonium chloride, dimethylaminoethyl acrylate methyl chloride quaternary salt, dimethylaminoethyl acrylate benzyl chloride quaternary salt, dimethylaminoethyl methacrylate methyl chloride quaternary salt, dimethylaminoethyl methacrylate benzyl chloride quaternary salt, methacrylamidopropyl trimethylammonium chloride, dimethylaminopropyl acrylamide methyl sulfate quaternary salt, dimethylaminopropyl acrylamide sulfuric acid salt, dimethylaminopropyl acrylamide hydrochloric acid salt, methacrylamidopropyltrimethylammonium chloride, dimethylaminopropyl methacrylamide methyl sulfate quaternary salt, dimethylaminopropyl methacrylamide sulfuric acid salt, dimethylaminopropyl methacrylamide hydrochloric acid salt, diethylaminoethylacrylate, diethylaminoethylmethacrylate, diallyldiethylammonium chloride, diallyldimethylammonium chloride, and the like.

In an embodiment, zwitterionic monomers are particularly suitable for use in neutral, acidic, alkaline and/or oxidizing cleaning compositions. Representative zwitterionic monomers include N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio] ethyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N, N-diallylamine ammonium betaine (MDABS), N,N-diallyl-N-methyl-N-(2-sulfoethyl)ammonium betaine, and the like.

In an aspect, the aqueous phase is prepared by mixing together in water one or more water-soluble monomers, and any polymerization additives such as inorganic or hydrophobic salts, chelants, pH buffers, processing aids, and the like. In an embodiment, the monomers are ethylenically unsaturated water-soluble or water-dispersible monomers and/or comonomers. In a further embodiment, the monomers are emulsified in a hydrophobic or hydrocarbon continuous oil phase by using oil- and/or water soluble initiators via radical polymerization, wherein the polymers may be nonionic, anionic, cationic, and/or zwitterionic. In a preferred embodiment, the monomers are selected from acrylamide or methacrylamide, such as acrylic acid or its salts, N-t-butyl acrylamide sulfonic acid (ATBS) or its salts, acrylamide tertiary butyl sulfonic acid or its salts, or 2-(acryloyloxy)-N,N,N-trimethylethananminium (DMAEA.MCQ). In a further preferred embodiment, the monomers are further selected from the group consisting of diallyldimethylammonium chloride, dimethylaminoethyl acrylate methyl chloride quaternary salt, acrylamidopropyltrimethylammonium chloride, dimethylaminoethyl methacrylate methyl chloride quaternary salt, methacrylamidopropyltrimethylammonium chloride, acrylic acid, sodium acrylate, ammonium acrylate, methacrylic acid, sodium methacrylate, and ammonium methacrylate.

In a preferred embodiment, the monomers are acrylamide and diallyldimethylammonium chloride. In a further preferred embodiment, the monomers are acrylamide and dimethylaminoethylacrylate methyl chloride quaternary salt. In a further preferred embodiment, the monomers are acrylamide, dimethylaminoethylacrylate benzyl chloride quaternary salt and dimethylaminoethylacrylate methyl chloride quaternary salt. Representative copolymers of acrylic acid and acrylamide useful as microparticles include Nalco® 8677 PLUS, available from Nalco Chemical Company, Naperville, Ill., USA. Other copolymers of acrylic acid and acrylamide are described in U.S. Pat. No. 5,098,520, incorporated herein by reference.

The degree of polymerization of monomers in the aqueous phase is determined by the change in the reaction density for water-in-oil emulsion polymerization, calorimeterically by measuring the heat of reaction, by quantitative infrared spectroscopy, or chromatographically, by measuring the level of unreacted monomer.

In an aspect, the aqueous phase is added to the oil phase (under high shear mixing or vigorous stirring) to form an emulsion.

The hydrophobic/hydrocarbon (or oil) phase is prepared by mixing together an inert hydrocarbon liquid with one or more oil soluble surfactants. The hydrophobic liquid is selected from the group consisting of benzene, xylene, toluene, mineral oils, kerosene, napthas, petroleums and combinations of the same. In a preferred aspect, the hydrophobic liquid is an isoparafinic hydrocarbon. The surfactant mixture should have a low HLB, to ensure the formation of an oil continuous emulsion. Appropriate surfactants for water-in-oil emulsion polymerizations, which are commercially available, are compiled in the North American Edition of McCutcheon's Emulsifiers & Detergents, which is incorporated by reference in its entirety.

In an aspect, the inverse emulsion polymer is a free-flowing liquid. An aqueous solution of the inverse emulsion polymer, in simplest methodology, can be generated by adding a desired amount of the emulsion polymer to water with vigorous mixing in the presence of a high-HLB surfactant as described in U.S. Pat. No. 3,734,873 which is herein incorporated by reference in its entirety.

An effective amount of the inverse emulsion polymer is provided to the cleaning compositions to provide ready-to-use reduced inhalation risk compositions having lower concentrations that conventional viscosity-modifying polymers. Beneficially, the inverse emulsion polymers are highly concentrated for dilution systems while maintaining viscoelasticity even for such highly concentrated formulations. Suitable concentrations of the inverse emulsion polymer in a concentrated formulation include between about 0.0001% and about 1% by weight, between about 0.0005% and about 0.5% by weight, between about 0.01% and about 0.2% by weight, and more preferably between about 5 ppm and 200 ppm active inverse emulsion polymer. Without being limited according to the invention, all ranges recited are inclusive of the numbers defining the range and include each integer within the defined range.

Dispersion Polymer

In an embodiment of the invention, the polymer component is a dispersion polymer. A dispersion polymer means a dispersion of fine particles of polymer in an aqueous salt solution, which is prepared by polymerizing monomers with stirring in an aqueous salt solution in which the resulting polymer is insoluble. See U.S. Pat. Nos. 8,992,688; 5,708,071; 4,929,655; 5,006,590; 5,597,859; 5,597,858 and European Patent nos. 657,478 and 630,909. In a typical procedure for preparing solution and gel polymers, an aqueous solution containing one or more water-soluble monomers and any additional polymerization additives such as chelants, pH buffers, and the like, is prepared. This mixture is charged to a reactor equipped with a mixer, a thermocouple, a nitrogen purging tube and a water condenser. The solution is mixed vigorously, heated to the desired temperature, and then one or more polymerization initiators are added. The solution is purged with nitrogen while maintaining temperature and mixing for several hours. Typically, the viscosity of the solution increases during this period. After the polymerization is complete, the reactor contents are cooled to room temperature and then transferred to storage. Solution and gel polymer viscosities vary widely, and are dependent upon the concentration and molecular weight of the active polymer component.

In an aspect of the invention, the dispersion polymer is a cationic, anionic or nonionic high molecular weight dispersion polymer.

Suitable concentrations of the dispersion polymer in a concentrated formulation include between about 0.0001% and about 1% by weight, between about 0.0005% and about 0.5% by weight, between about 0.01% and about 0.2% by weight, and more preferably between about 5 ppm and 200 ppm active dispersion polymer. Without being limited according to the invention, all ranges recited are inclusive of the numbers defining the range and include each integer within the defined range.

Powder Polymer

In an embodiment of the invention, the polymer component is formulated as a dried or powder polymer. In one example, the polymer component includes a mixture of polyethylene oxide (PEO), polyacrylamide, and polyacrylate. In a further example, the polymer component includes mixtures of PEO and polyacrylamide. PEO is a high molecular weight polymer. A suitable PEO can have a molecular weight between about 3,000,000 and about 7,000,000. One commercially available PEO is Polyox WSR 301, which has a molecular weight of about 4,000,000 and is available from Dow. A suitable concentration range for PEO is between approximately 0.01 wt.-% and 0.3 wt.-% of the concentrate cleaning solution. A particular suitable concentrate range for PEO is between approximately 0.01 wt.-% and 0.2 wt.-% of the concentrate cleaning solution.

The polymer component may alternatively or additionally include a polyacrylamide. A suitable polyacrylamide can have a molecular weight between about 8 million and 16 million, and more suitably between about 11 million and 13 million. One commercially available polyacrylamide is SuperFloc® N-300 available from Kemira Water Solutions, Inc. A suitable concentration range for polyacrylamide is between approximately 0.01 wt.-% and 0.3 wt.-% of the concentrate cleaning solution. A particularly suitable concentration range for polyacrylamide is approximately 0.01 wt.-% and 0.2 wt.-% of the concentrate cleaning solution.

Polyacrylate is a high molecular weight polymer. A suitable polyacrylate polymer can have a molecular weight between about 500,000 and about 3 million. A more suitable polyacrylate polymer can have a molecular weight of at least about 1 million. One commercially available polyacrylate is Aquatreat® AR-7H available from Akzo Nobel. Suitable polyacrylate concentrations in the concentrate composition are between about 0.5 wt.-% to about 20 wt.-%. Particularly suitable polyacrylate concentrations in the concentrate composition are between about 1 wt.-% and about 10 wt.-%.

In a further embodiment of the invention, other known suitable polymers may be formulated as dried polymer, or powders for inclusion in the cleaning compositions according to the invention. Examples of such suitable polymers can be found in U.S. Pat. Nos. 9,127,241 and 9,206,281, which are incorporated by reference in their entirety.

Xanthan Gum

In an aspect of the invention, the polymer component is xanthan gum. Xanthan is an extracellular polysaccharide of *xanthomonas* campestras. Xanthan is made by fermentation based on corn sugar or other corn sweetener by-products. Xanthan comprises a poly beta-(1→4)-D-Glucopyranosyl backbone chain, similar to that found in cellulose. Aqueous dispersions of xanthan gum and its derivatives exhibit novel and remarkable rheological properties. Low concentrations of the gum have relatively high viscosity which permit it economical use and application. Xanthan gum solutions exhibit high pseudoplasticity, i.e. over a wide range of concentrations, rapid shear thinning occurs that is generally understood to be instantaneously reversible. Non-sheared materials have viscosity that appears to be independent of the pH and independent of temperature over wide ranges. Preferred xanthan materials include crosslinked xanthan materials. Xanthan polymers can be crosslinked with a variety of known covalent reacting crosslinking agents reactive with the hydroxyl functionality of large polysaccharide molecules and can also be crosslinked using divalent, trivalent or polyvalent metal ions. Such crosslinked xanthan gels are disclosed in U.S. Pat. No. 4,782,901, which patent is incorporated by reference herein. Suitable crosslinking agents for xanthan materials include metal cations such as $Al+3$, $Fe+3$, $Sb+3$, $Zr+4$ and other transition metals, etc. Known organic crosslinking agents can also be used. The preferred crosslinked xanthan agent of the invention is KELZAN AR, a product of Kelco, a division of Merck Incorporated. KELZAN AR is a crosslinked xanthan that provides a thixotropic cleaner that can produce large particle size mist or aerosol when sprayed.

Suitable concentrations of the xanthan gum in a concentrated solution include between about 0.0001% and about 1% by weight, between about 0.0005% and about 0.5% by weight, between about 0.01% and about 0.2% by weight, and more preferably between about 5 ppm and 200 ppm xanthan gum. Without being limited according to the invention, all ranges recited are inclusive of the numbers defining the range and include each integer within the defined range.

Acid Component

The cleaning compositions according to the invention optionally include at least one acid component. In other aspects, the cleaning compositions include at least two acid components. The cleaning compositions according to the invention optionally include at least one acid component when the cleaning component is a quaternary ammonium compound. Without seeking to be limited to particular theory of the invention, it is believed that the inclusion of an acid component maintains the pH of the cleaning compositions at an acidic pH, thus allowing the quaternary ammonium compound to come into contact with biological matter, such as lung tissue, reducing the risks of inhalation, namely risk of toxicity. Under mild acidic conditions, biological matter may be at or near their respective isoelectric points. Thus, reducing electrostatic interactions between positively charged cleaning compounds or quaternary ammonium compounds with negatively or partially negatively charged biological matter reduces the risk of toxicity and the inhalation risks associated with cleaning compounds or quaternary ammonium compounds. Further, inclusion of an acid component within a cleaning compounds or quaternary ammonium compound based cleaning composition is unexpected as cleaning compounds or quaternary ammonium compounds typically retain their function best neutral or alkaline pH. In an aspect of the invention, the acid component is any compound capable of acting as a proton donor. In a further aspect of the invention, the acid component is a mineral acid, organic acid, carboxylic acid, amino acid, acidic chelant, and/or a compound capable of acting as a proton donor.

In a further aspect of the invention, at least two acid components are used in compositions according to the invention. Suitable acid components include carboxylic acids, mineral acids, organic acids, amino acid, acidic chelants, fatty acids, fatty acid surfactants, and/or a compound capable of acting a proton donor, wherein the components may be at least two identical components of any suitable acid component classification, at least two components of any suitable acid component classification, or at least one component of any suitable acid classification and at least one component of any different, yet still suitable acid classification.

In an aspect, the concentrate compositions include from about 0.1 wt.-%-30 wt.-% of an acid component, preferably from about 0.1 wt.-%-25 wt.-% of an acid component, and more preferably from about 1.0 wt.-%-20 wt.-% of an acid component. In addition, without being limited according to the invention, all ranges recited are inclusive of the numbers defining the range and include each integer within the defined range.

Carboxylic Acid

In an aspect of the invention, the acid component is a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxyl groups. Carboxylic acids have a tendency to acidify aqueous compositions in which they are present as the hydrogen atom of the carboxyl group is active and may appear as an anion. The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH. Examples of such carboxylic acids include, but are not limited to, acetic acid, citric acid, succinic acid, adipic acid, hydroxyacetic acid, and lactic acid. One of skill in the art will appreciate that other carboxylic acids may be used for purposes of the invention.

Mineral Acid

In an aspect of the invention, the acid component is a mineral acid, i.e., an inorganic acid. Examples of such mineral acids include, but are not limited to, phosphoric acid, sulfamic acid, sulfuric acid, nitric acid, and hydrocholoric acid. Generally, all mineral acids form hydrogen ions and the conjugate base ions when dissolved in water. For example, sulfuric acid forms hydrogen sulfate in aqueous solutions via complete ionization to form hydronium ions and hydrogen sulfate. Such conjugate bases are also useful acid components for purposes of the invention.

Organic Acid

In an aspect of the invention, the acid component is an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof.

Amino Acid

In an aspect of the invention, the acid component is an amino acid and/or an amino acid derivative. Generally, an amino acid contains an amine functional group and a carboxylic acid functional group, usually along with a side chain group to each amino acid. Suitable amino acid and/or amino acid derivatives include, but are not limited to alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, selenocysteine, pyrrolysine, and derivatives thereof.

Acidic Chelant

In an aspect of the invention, the acid component is an acidic chelant. Chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale. The ligand forms a chelate complex with the substrate. The term is reserved for complexes in which the metal ion is bound to two or more atoms of the chelant. The chelants for use in the present invention are those having the capability to act a proton donor.

Suitable chelating agents can be selected from the group consisting of amino carboxylates, amino phosphonates, polyfunctionally-substituted aromatic chelating agents and mixtures thereof. Preferred chelants for use herein are chelants such as the amino acids based chelants and preferably citrate, citrate, tararate, and glutamic-N,N-diacetic acid and derivatives and/or phosphonate based chelants and preferably diethylenetriamine penta methylphosphonic acid.

Amino carboxylates include ethylenediaminetetra-acetates, N-hydroxyethylethylenediaminetriacetates, nitrilotriacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein. As well as MGDA (methyl-glycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred.

Other suitable chelants include amino acid based compound or a succinate based compound. The term "succinate based compound" and "succinic acid based compound" are used interchangeably herein. Other suitable chelants are described in U.S. Pat. No. 6,426,229. Particular suitable chelants include; for example, aspartic acid-N-monoacetic acid (ASMA), aspartic acid-N,N-diacetic acid (ASDA), aspartic acid-N-monopropionic acid (ASMP), iminodisuccinic acid (IDS), Imino diacetic acid (IDA), N-(2-sulfomethyl)aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), alanine-N,N-diacetic acid (ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof. Also suitable is ethylenediamine disuccinate ("EDDS"), especially the [S,S] isomer as described in U.S. Pat. No. 4,704,233. Furthermore, Hydroxyethyleneiminodiacetic acid, Hydroxyiminodisuccinic acid, Hydroxyethylene diaminetriacetic acid is also suitable. Particularly preferred is alanine. N,N-bis(carboxymethyl)-, trisodium salt.

Other chelants include homopolymers and copolymers of polycarboxylic acids and their partially or completely neutralized salts, monomeric polycarboxylic acids and hydroxycarboxylic acids and their salts. Preferred salts of the abovementioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least two carboxyl groups which are in each case separated from one another by, preferably, no more than two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulfonates.

Amino phosphonates are also suitable for use as chelating agents and include ethylenediaminetetrakis(methylenephosphonates) as DEQUEST. Preferred, these amino phosphonates that do not contain alkyl or alkenyl groups with more than about 6 carbon atoms.

Polyfunctionally-substituted aromatic chelating agents are also useful in the compositions herein such as described in U.S. Pat. No. 3,812,044. Preferred compounds of this type in acid form are dihydroxydisulfobenzenes such as 1,2-dihydroxy-3,5-disulfobenzene.

Further suitable polycarboxylates chelants for use herein include citric acid, lactic acid, acetic acid, succinic acid, formic acid all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

Fatty Acids and Fatty Acid Surfactants

In an aspect of the invention, the acid component is a fatty acid and/or fatty acid surfactant. As used herein, the term "fatty acid" includes any of a group of carboxylic acids that include an alkyl chain. In some embodiments, the alkyl groups can be linear or branched, and saturated or unsaturated. The chain of alkyl groups contains any length of carbon atoms. In some embodiments, the chain of alkyl groups contains from 4 to 12 carbon atoms, 5 to 11 carbon atoms, or 8 to 10 carbon atoms. Exemplary fatty acids can be selected from hexanoic acid, heptanoic acid, octanoic acid, nonanoic acid, decanoic acid, lauric acid, palmitic acid, stearic acid, oleic acid, caproic acid, caprylic acid, capric acid and mixtures thereof. Exemplary longer alkyl chain fatty acids can be selected from for example myristic acid, arachidic acid, behenic acid, lignoceric acid, cerotic acid, myristoleic acid, palmitoleic acid, sapienic acid, elaidic acid, vaccenic acid, linoleic acid, linoelaidic acid, a-linolenic acid, arachidonic acid, eicosapentaenoic acid, erucic acid, decosahexaenoic acid, gadoleic acid, erucic acid, margaric acid, behenic acid, ricinoleic acid, lignoceric acid, licanic acid, eleostearic acid and mixtures thereof.

In a further aspect, of the invention the acid component is a fatty acid surfactant. Various exemplary surfactants which are fatty acids are disclosed in the following section.

Additional Surfactants

In some embodiments, the compositions of the present invention optionally include a surfactant. Surfactants suitable for use with the compositions of the present invention include, but are not limited to, nonionic surfactants, anionic surfactants, and amphoteric surfactants. In some embodiments, the concentrated compositions of the present invention include about 0 wt.-% to about 30 wt.-% of a surfactant. In other embodiments the concentrated compositions of the present invention include about 0.1 wt.-% to about 30% of a surfactant. In still yet other embodiments, the concentrated compositions of the present invention include about 0.5 wt.-% to about 10 wt.-% of a surfactant.

Nonionic Surfactants

Useful additional nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available from BASF Corp. One class of compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Another class of compounds are tetra-functional block copolymers derived from the sequential addition of propylene oxide and ethylene oxide to ethylenediamine. The molecular weight of the propylene oxide hydrotrope ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton' manufactured by Union Carbide.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Lutensol™, Dehydol™ manufactured by BASF, Neodol™ manufactured by Shell Chemical Co. and Alfonic™ manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Disponil or Agnique manufactured by BASF and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:
Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

The alkylphenoxypolyethoxyalkanols of U.S. Pat. No. 2,903,486 issued Sep. 8, 1959 to Brown et al. and represented by the formula

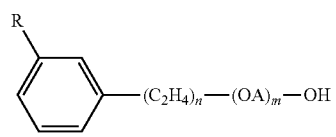

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkylene oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula Y[(C$_3$H$_6$O$_n$ (C$_2$H$_4$O)$_m$H]$_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: P[(C$_3$H$_6$O)$_n$ (C$_2$H$_4$O)$_m$H]$_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula R$_2$CON$_{R1}$Z in which: R1 is H, C$_1$-C$_4$ hydrocarbyl, 2-hydroxy ethyl, 2-hydroxy propyl, ethoxy, propoxy group, or a mixture thereof; R$_2$ is a C$_5$-C$_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated C$_6$-C$_{18}$ fatty alcohols and C$_6$-C$_{18}$ mixed ethoxylated and propoxylated fatty alcohols are suitable surfactants for use in the present compositions, particularly those that are water soluble. Suitable ethoxylated fatty alcohols include the C$_6$-C$_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: R$_6$CON (R$_7$)$_2$ in which R$_6$ is an alkyl group containing from 7 to 21 carbon atoms and each R$_7$ is independently hydrogen, C$_1$-C$_4$ alkyl, C$_1$-C$_4$ hydroxyalkyl, or —(C$_2$H$_4$O)xH, where x is in the range of from 1 to 3.

A useful class of non-ionic surfactants include the class defined as alkoxylated amines or, most particularly, alcohol alkoxylated/aminated/alkoxylated surfactants. These nonionic surfactants may be at least in part represented by the general formulae: R$^{20}$—(PO)$_s$N—(EO)$_t$H, R$^{20}$—(PO)$_s$N—(EO)$_t$H(EO)$_t$H, and R$^{20}$—N(EO)$_t$H; in which R$^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: R$^{20}$—(PO)$_v$—N [(EO)$_w$H][(EO)$_z$H] in which R$^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise Nonionic Surfactants, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents is another class of additional nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

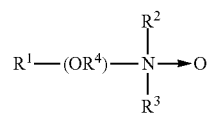

wherein the arrow is a conventional representation of a semi-polar bond; and, R$^1$, R$^2$, and R$^3$ may be aliphatic, aromatic, heterocyclic, alicyclic, or combinations thereof. Generally, for amine oxides of detergent interest, R$^1$ is an alkyl radical of from about 8 to about 24 carbon atoms; R$^2$ and R$^3$ are alkyl or hydroxyalkyl of 1-3 carbon atoms or a mixture thereof; R$^2$ and R$^3$ can be attached to each other, e.g. through an oxygen or nitrogen atom, to form a ring structure; R$^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

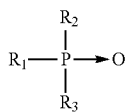

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

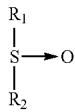

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R—(EO)$_5$(PO)$_4$) and Dehypon LS-36 (R—(EO)$_3$(PO)$_6$); and capped alcohol alkoxylates, such as Plurafac LF221 and Tegoten EC11; mixtures thereof, or the like.

Anionic Surfactants

Also useful in the present invention are additional surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R\text{—}O\text{—}(CH_2CH_2O)_n(CH_2)_m\text{—}CO_2X \qquad (3)$$

in which R is a $C_8$ to $C_{22}$ alkyl group or

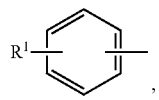
, in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

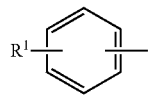

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

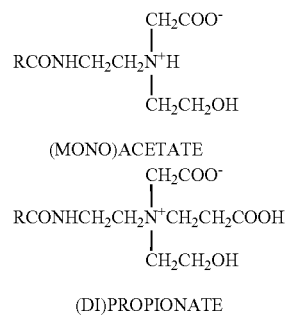

Neutral pH Zwitterion

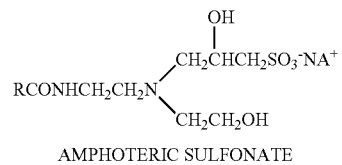

AMPHOTERIC SULFONATE wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$ $(CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong" inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

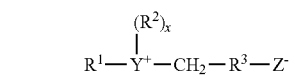

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

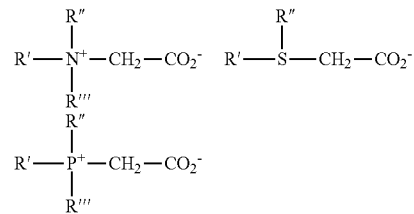

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6-C_{18}$ hydrocarbyl group, each $R^1$ is typically independently $C_1-C_3$ alkyl, e.g. methyl, and $R^2$ is a $C_1-C_6$ hydrocarbyl group, e.g. a $C_1-C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Additional Functional Ingredients

The components of the cleaning composition can further be combined with various functional components suitable for use in disinfecting and sanitizing applications. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in cleaning. However, other embodiments may include functional ingredients for use in other applications.

In other embodiments, the compositions may include defoaming agents, anti-redeposition agents, bleaching agents, solubility modifiers, dispersants, metal protecting agents, stabilizing agents, corrosion inhibitors, additional sequestrants and/or chelating agents, fragrances and/or dyes, rheology modifiers or thickeners, hydrotropes or couplers, buffers, solvents and the like.

EXEMPLARY EMBODIMENTS

Exemplary ranges of the cleaning compositions according to the invention in concentrated compositions are shown in Table 3 each in weight percentage.

TABLE 3

| Material | First Exemplary Range wt.-% | Second Exemplary Range wt.-% | Third Exemplary Range wt.-% |
| --- | --- | --- | --- |
| Cleaning Component | 1-15 | 0.1-10 | 0.001-0.04 |
| Polymer Component | 0.0005-0.5 | 0.001-0.2 | 0.0001-0.2 |
| Acid Component | 0-30 | 0.1-25 | 1-20 |
| Surfactant | 0-30 | 0.1-30 | 0.5-10 |
| Additional Optional Functional Ingredients | Remainder | Remainder | Remainder |

According to the invention, the concentrated cleaning compositions set forth in Table 3 have any suitable pH for application of use, including from about 1 to 12. However, according to aspects of the invention, the concentrated solution preferably has an acidic to neutral pH depending on a particular application of use thereof, including from about 0 to 6. Without limiting the scope of invention, the numeric ranges are inclusive of the numbers defining the range and include each integer within the defined range.

The cleaning compositions may include concentrate compositions or may be diluted to form use compositions. In general, a concentrate refers to a composition that is intended to be diluted with water to provide a use solution that contacts an object to provide the desired cleaning, rinsing, or the like. The cleaning composition that contacts the articles to be washed or cleaned can be referred to as a concentrate or a use composition (or use solution) dependent upon the formulation employed in methods according to the invention. It should be understood that the concentration of the quaternary ammonium compound, acid component, surfactant, and other optional functional ingredients in the detergent composition will vary depending on whether the cleaning composition is provided as a concentrate or as a use solution.

A use solution may be prepared from the concentrate by diluting the concentrate with water at a dilution ratio that provides a use solution having desired detersive properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

Manufacturing Methods

Compositions of the invention are prepared by addition of materials. The anionic surfactant is added to the quaternary ammonium. The quaternary ammonium compound readily couples the more hydrophobic organic acid into solution with minimal or no agitation.

In some aspects, the compositions according to the invention can be made by combining the components in an aqueous diluent using commonly available containers and blending apparatus. Beneficially, no special manufacturing equipment is required for making the compositions employing the quaternary ammonium compounds and the anionic surfactants. A preferred method for manufacturing the cleaning composition of the invention includes introducing the components into a stirred production vessel.

The cleaning compositions according to the invention can be provided in single use or multiple use compositions. In a preferred aspect, the composition is a concentrated liquid composition.

Methods Employing Cleaning Compositions of the Invention

The present invention includes methods of using the cleaning compositions of the present invention for various applications. The invention includes a method for reducing a microbial population, a method for reducing the population of a microorganism on skin and a method for treating a disease of skin. These methods can operate on an article, surface, in a body or stream of water or a gas, or the like, by contacting the article, surface, body, or stream with a composition of the invention. Contacting can include any of numerous methods for applying a composition of the invention, such as spraying the compositions, immersing the article in compositions, foam or gel treating the article with the compounds or composition, or a combination thereof.

In some embodiments, the compositions of the present invention include killing one or more of the pathogenic bacteria associated with health care surfaces and environments including, but not limited to, *Salmonella typhimurium, Staphylococcus aureus*, methicillin resistant *Staphylococcus aureus, Salmonella choleraesurus, Pseudomonas aeruginosa, Escherichia coli*, mycobacteria, yeast, and mold. The compositions of the invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compounds and compositions of the present invention, as described above, have activity against a wide variety of human pathogens. The present compounds and compositions can kill a wide variety of microorganisms on a food processing surface, on the surface of a food product, in water used for washing or processing of food product, on a health care surface, or in a health care environment.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10. In still other embodiments, the present methods can be used to reduce the microbial population in and/or on the target or the treated target composition by at least five log 10. Without limiting the scope of invention, the numeric ranges are inclusive of the numbers defining the range and include each integer within the defined range.

The compositions of the invention can be used for a variety of domestic or industrial applications, e.g., to reduce microbial or viral populations on a surface or object or in a body or stream of water. The compounds can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compounds can be employed as a foaming or non-foaming environmental sanitizer or disinfectant.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, lubricants, rinse aids, 2-in-1 and/or 3-in-1 products, such as insecticide/cleaner/sanitizer, 3-sink applications, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

In some aspects, the compositions of the present invention can be employed for reducing the population of pathogenic microorganisms, such as pathogens of humans, animals, and the like. The compounds exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. Compositions of the present invention can reduce the population of microorganisms on skin or other external or mucosal surfaces of an animal. In addition, the present compounds can kill pathogenic microorganisms that spread through transfer by water, air, or a surface substrate. The compositions need only be applied to the skin, other external or mucosal surfaces of an animal water, air, or surface.

The cleaning compositions can also be used on foods and plant species to reduce surface microbial populations; used at manufacturing or processing sites handling such foods and plant species; or used to treat process waters around such sites. For example, the compounds can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compounds of the invention include eggs, meats, seeds, leaves, fruits and vegetables. Particular plant surfaces include both harvested and growing leaves, roots, seeds, skins or shells, stems, stalks, tubers, corms, fruit, and the like.

In some aspects, the compositions of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

Compositions of the present invention can also be employed by dipping food processing equipment into the use solution, soaking the equipment for a time sufficient to sanitize the equipment, and wiping or draining excess solution off the equipment, The compound may be further employed by spraying or wiping food processing surfaces with the use solution, keeping the surfaces wet for a time sufficient to sanitize the surfaces, and removing excess solution by wiping, draining vertically, vacuuming, etc.

Compositions of the present invention may also be used in a method of sanitizing hard surfaces such as institutional type equipment, utensils, dishes, health care equipment or tools, instruments and other hard surfaces.

The cleaning compositions can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a compound, such as spraying the compound, immersing the object in the compound, foam or gel treating the object with the compound, or a combination thereof.

A concentrate or use concentration of a compound of the present invention can be applied to or brought into contact with an object by any conventional method or apparatus for applying an antimicrobial or cleaning compound to an object. For example, the object can be wiped with, sprayed with, foamed on, and/or immersed in the compound, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compounds according to the invention, or solutions containing these compounds.

The various methods of treatment according to the invention can include the use of any suitable level of the cleaning compound. In some embodiments, the treated target composition comprises from about 1 ppm to about 1000 ppm of the cleaning compound when diluted for use. In further embodiments, the treated target composition comprises from about 1 ppm and about 500 ppm, 5 ppm and about 400 ppm, 10 ppm and about 100 ppm, 20 ppm and about 100 ppm, 25 ppm and about 100 ppm, 10 ppm and about 75 ppm, 20 ppm and about 75 ppm, 25 ppm and about 75 ppm, or about 50 ppm of the cleaning compound when diluted for use.

In an aspect, the methods of the invention include generating a use solution from the concentrated solid or liquid compositions of the invention. A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In an aspect, a concentrated cleaning composition is diluted to use solution concentration of about 0.001% (wt/vol.) to about 10% (wt/vol.), or from about 0.001% (wt/vol.) to about 5% (wt/vol.), or from about 0.001% (wt/vol.) to about 2% (wt/vol.), or from about 0.01% (wt/vol.) to about 1% (wt/vol.). Without limiting the scope of invention, the numeric ranges are inclusive of the numbers defining the range and include each integer within the defined range.

Compositions of the invention can be formulated and sold for use as is, or as solvent or solid concentrates. If desired, such concentrates can be used full-strength as sanitizing rinse compositions. However, the concentrates typically will be diluted with a fluid (e.g., water) that subsequently forms the dilute phase or a use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

The various applications of use described herein provide the cleaning compositions to a surface and/or water source. Beneficially, the compositions of the invention are fast-acting. However, the present methods require a certain minimal contact time of the compositions with the surface or product in need of treatment for occurrence of sufficient antimicrobial effect. The contact time can vary with concentration of the use compositions, method of applying the use compositions, temperature of the use compositions, pH of the use compositions, amount of the surface or product to be treated, amount of soil or substrates on/in the surface or product to be treated, or the like. The contact or exposure time can be about 15 seconds, at least about 15 seconds, about 30 seconds or greater than 30 seconds. In some embodiments, the exposure time is about 1 to 5 minutes. In other embodiments, the exposure time is a few minutes to hours. In other embodiments, the exposure time is a few hours to days. The contact time will further vary based upon the use concentration of actives of compositions according to the invention.

Kits for Applications of Use

According to various applications of the compositions according to the invention a kit may be provided for dosing a composition according to the invention. In a particular application, the compositions may be provided by employing a kit according to embodiments of the invention. A kit for dosing and/or providing a cleaning composition according to the invention may comprise, consist of and/or consist essentially of a cleaning component and polymer component (and/or surfactant and/or acid component). Alternatively, the kits may comprise, consist of and/or consist essentially of a polymer component (and/or surfactant and/or acid component) for dosing with a cleaning component in an application of use. The kit may further comprise a measuring means and/or a dosing means.

The kit may further comprise additional elements. For example, a kit may also include instructions for use of the cleaning compositions. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions. The various components of the kit optionally are provided in suitable containers as necessary, e.g., a bottle, jar or vial.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. Commercial Product A is formulated to include the following raw materials.

The materials used in the following Examples are provided herein:

Commercial Product A: mixture of alkylbenzyl ammonium chloride and dialkyl dimethyl ammonium chloride Polymer Component A: cationic flocculant Commercial Product B: mixture of alkylbenzyl ammonium chloride and dialkyl dimethyl ammonium chloride

Example 1

Comparative studies on the spray pattern of a commercially available quaternary ammonium chloride with and without the addition of a polymer. Test compositions are shown in Table 4 Composition A is formulated according to the present invention.

TABLE 4

| Description | wt % Active Quat | Wt % Polymer Component A |
|---|---|---|
| Commercial product A | 7.5 | 0.0 |
| Composition A | 7.5 | 0.05 |

Results from the spray pattern comparison indicated that the formulations according to the present invention provided a stream with a wide spray pattern as opposed to a fine mist with a wide spray pattern. The presence of the polymer component therefore reduces the misting particles and thereby reduces the inhalation risks.

Example 2

Commercially available quat sanitizers were tested versus a composition according to the claimed invention. Test were performed in water with 500 ppm hardness at a temperature of 77° F. Samples contaminated with *E. coli* and *Staph* were contacted with each of the compositions for 30 seconds. Composition B is formulated according to the present invention. Results are shown in Table 5.

TABLE 5

| Composition | E. coli Survivors CFU/mL Rep 1 | E. coli Survivors CFU/mL Rep 2 | Staph Survivors CFU/mL Rep 1 | Staph Survivors CFU/mL Rep 12 | E. Coli Avg. Log Reduction | Staph Avg. Log Reduction |
|---|---|---|---|---|---|---|
| Commercial Product B | 1e1 | 1e1 | 1e1 | 1e1 | >6.28 | >6.38 |
| Composition B | 1e1 | 1e1 | 1e1 | 1e1 | >6.28 | >6.38 |

From the results shown in Table 5, the inclusion of the polymer component does not adversely affect micro efficacies. The inclusion of the polymer component provides a reduced misting profile which leads to the quat remaining on the surface to be treated longer. As such, the addition of the polymer component imparts enhanced residual kill.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A concentrated cleaning composition, consisting essentially of:

from about 1 wt. % to about 15 wt. % of a cleaning component, wherein the cleaning component is an acid sanitizer comprising a carboxylic acid, peracid, mineral acid, organic acid, amino acid, fatty acid, or linear alkylbenzene, a quaternary ammonium compound antimicrobial agent having the formula:

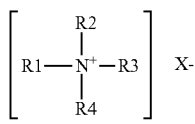

wherein groups R1, R2, R3, and R4 each have less than a C20 chain length, and X— is an anionic counterion; or a combination thereof; and from about 0.0005 wt. % to about 0.5 wt. % of a polymer component, wherein the polymer is a high molecular weight cationic, nonionic, or anionic inversion emulsion polymer; a high molecular weight cationic, anionic, or nonionic dispersion polymer; or a combination thereof;

from about 0.1 wt. % to about 30 wt. % of an acid component comprising a mineral acid, an organic acid, a carboxylic acid, an amino acid, a fatty acid, or a combination thereof, wherein the acid component provides pH control so that the cleaning composition has a pH of from about 0 to about 6;

a solvent consisting of an EO/PO block copolymer, an alcohol alkoxylate according to the formula R—$(EO)_5(PO)_4$ wherein R is a C12-C14 alkyl group, an alcohol alkoxylate according to the formula R—$(EO)_3(PO)_6$ wherein R is a C12-C14 alkyl group, water, or a combination thereof; and optionally one or more additional functional ingredients comprising a surfactant, thickener, viscosity modifier, humectant, metal protecting agent, stabilizing agent, corrosion inhibitor, sequestrant, chelating agent, solidifying agent, sheeting agent, fragrance, dye, hydrotrope, coupler, or a combination thereof;

wherein the composition has a viscosity of 50 to 5000 cPs;

wherein the composition provides at least 4 log kill on treated surfaces while providing reduced inhalation risk; and wherein the composition provides reduced inhalation risk with a median particle size of about 11 microns or greater.

2. The cleaning composition of claim 1, wherein the polymer component is a high molecular weight cationic or anionic inversion emulsion polymer.

3. The cleaning composition of claim 1, wherein the polymer component is a high molecular weight cationic or anionic dispersion polymer.

4. The cleaning composition of claim 1, wherein the polymer component is a powder.

5. The cleaning composition of claim 1, wherein the polymer component has a molecular weight of 1 million Da to 25 million Da and a particular size ranging from 0.1 to 10 microns.

6. The cleaning composition of claim 1, wherein the acid component is present in an amount of about 30 wt.-%.

7. The cleaning composition of claim 1, wherein the surfactant is an anionic surfactant, nonionic surfactant, amphoteric surfactant, or a combination thereof, and wherein the surfactant is present in an amount from about 0.1 wt.-% to about 30 wt.-%.

8. A method of reducing a microbial population comprising: applying to a substrate the cleaning composition of claim 1; wherein the composition has a viscosity of 50 to 5000 cPs and provides at least 4 log kill on treated surfaces while providing a reduced inhalation risk; and wherein the microbial population comprises *Salmonella typhimurium, Staphylococcus aureus, Salmonella choleraesurus, Pseudomonas aeruginosa, Listeria monocytogenes, Escherichia coli, Streptococci, Legionalla*, or a combination thereof.

* * * * *